US009982243B2

(12) United States Patent
Berghard et al.

(10) Patent No.: US 9,982,243 B2
(45) Date of Patent: May 29, 2018

(54) MODIFIED SULFAMIDASE AND PRODUCTION THEREOF

(71) Applicant: Swedish Orphan Biovitrum AB (publ), Stockholm (SE)

(72) Inventors: Charlotta Berghard, Stockholm (SE); Erik Nordling, Danderyd (SE); Stefan Svensson Gelius, Älvsjö (SE); Agneta Tjernberg, Stockholm (SE)

(73) Assignee: SWEDISH ORPHAN BIOVITRUM AB (PUBL), Stockholm (SE)

( * ) Notice: Subject to any disclaimer, the term of this patent is extended or adjusted under 35 U.S.C. 154(b) by 75 days.

(21) Appl. No.: 14/806,504

(22) Filed: Jul. 22, 2015

(65) Prior Publication Data
US 2016/0230155 A1 Aug. 11, 2016

Related U.S. Application Data

(63) Continuation of application No. PCT/EP2015/057256, filed on Apr. 1, 2015.

(30) Foreign Application Priority Data

Apr. 1, 2014 (EP) .................................... 14162996

(51) Int. Cl.
A61K 38/00 (2006.01)
C12N 9/14 (2006.01)
C12N 9/96 (2006.01)

(52) U.S. Cl.
CPC ............. *C12N 9/14* (2013.01); *C12N 9/96* (2013.01); *C12Y 310/01001* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,863,782 A | 1/1999 | Hopwood et al. | |
| 5,972,333 A | 10/1999 | Hopwood et al. | |
| 6,200,563 B1 | 3/2001 | Hopwood et al. | |
| 6,458,579 B2 | 10/2002 | Hopwood et al. | |
| 6,491,913 B2 | 12/2002 | Hopwood et al. | |
| 2004/0006008 A1 | 1/2004 | LeBowitz et al. | |
| 2004/0122216 A1 | 6/2004 | Nielsen et al. | |
| 2005/0008635 A1 | 1/2005 | Graves et al. | |
| 2009/0041741 A1* | 2/2009 | Sly ..................... | C12N 9/2402 424/94.5 |
| 2010/0015684 A1 | 1/2010 | DeFrees et al. | |
| 2014/0205584 A1* | 7/2014 | Schuchman ........... | A61K 38/46 424/94.6 |
| 2014/0377246 A1 | 12/2014 | Tomatsu et al. | |

FOREIGN PATENT DOCUMENTS

| | | |
|---|---|---|
| WO | WO-2003/032913 | 4/2003 |
| WO | WO-2008/109677 | 9/2008 |
| WO | WO-201285622 | 6/2012 |
| WO | WO-2014/194427 | 12/2014 |
| WO | WO-2015/150490 | 10/2015 |

OTHER PUBLICATIONS

Ward et al. (Can. J. Chem. 67, 1206 (1989)).*
Sidhu et al. (Acta Crystallogr D Biol Crystallogr. May 1, 2014; 70(Pt 5): 1321-1335).*
Reusch (Periodate cleavage of 1,2-diols (glycols), 2015).*
Ramachandran et al. (Clin Proteomics. Dec. 2008 ; 4(3-4): 80-104).*
McMurry (Organic Chemistry, 8th Edition, 2012).*
Bailon et al. (Methods in Molecular Biology, vol. 147, 2000).*
Cox et al., "The cellular pathology of lysosomal diseases," J Pathol (2012) 226(2):241-254.
Fuller et al., "Disease-specific markers for the mucopolysaccharidoses," Pediatr Res (2004) 56(5):733-738.
Huynh et al., "Biochemical evidence for superior correction of neuronal storage by chemically modified enzyme in murine mucopolysaccharidosis VII," Proc Natl Acad Sci USA (2012) 109(42):17022-17027.
Grubb et al., "Chemically modified beta-glucuronidase crosses blood-brain barrier and clears neuronal storage in murine mucopolysaccharidosis VII," Proc Natl Acad Sci USA (2008) 105(7):2616-2621.
International Search Report and Written Opinion for PCT/EP2015/057256, dated Jun. 26, 2015, 13 pages.
Kim et al., "Carbohydrate recognition by the mannose-6-phosphate receptors," Curr Opin Struct Biol (2009) 19(5):534-542.
Kristiansen et al., "Periodate oxidation of polysaccharides for modification of chemical and physical properties," Carbohydr Res (2010) 345(10):1264-1271.
Mason et al., "Characterization of sulfated oligosaccharides in mucopolysaccharidosis type IIIA by electrospray ionization mass spectrometry," Anal. Chem (2006) 78(13):4534-4542.
Mason et al., "Distribution of Heparan Sulfate Oligosaccharides in Murine Mucopolysaccharidosis Type IIIA," Metabolites (2014) 4(4):1088-1100.

(Continued)

*Primary Examiner* — Jennifer Pitrak McDonald
*Assistant Examiner* — Sergio Coffa
(74) *Attorney, Agent, or Firm* — Morrison & Foerster LLP

(57) ABSTRACT

Disclosed herein are a modified sulfamidase, a composition comprising a modified sulfamidase, as well as methods for preparing a modified sulfamidase and therapeutic use of such a sulfamidase. In particular, the present disclosure relates to a modified sulfamidase comprising substantially no epitopes for glycan recognition receptors, thereby enabling transportation of said sulfamidase across the blood brain barrier of a mammal, wherein said sulfamidase has catalytic activity in the brain of said mammal.

13 Claims, 13 Drawing Sheets

(56) References Cited

OTHER PUBLICATIONS

Meng et al., "Systemic administration of tripeptidyl peptidase I in a mouse model of late infantile neuronal ceroid lipofuscinosis: effect of glycan modification," PLoS One (2012) 7(7):40509.

Neufeld et al., "The uptake of enzymes into lysosomes: an overview," Birth Defects Orig Artic Ser (1980) 16(1):77-84.

Omichi et al., "Preparation of neuraminidase-resistant human alpha 1-protease inhibitor and its clearance in rat blood circulation," Int J Biochem (1983) 15(11):1345-1351.

Ramsay et al., "Determination of monosaccharides and disaccharides in mucopolysaccharidoses patients by electrospray ionisation mass spectrometry," Mol Genet Metab (2003) 78(3):193-204.

Recksiek et al., "Sulfatases, trapping of the sulfated enzyme intermediate by substituting the active site formylglycine," J Biol Chem (1998) 273(11):6096-6103.

Rosenberg et al., "Effects of protein aggregates: an immunologic perspective," AAPS J (2006) 8(3):E501-507.

Rozaklis et al., "Impact of high-dose, chemically modified sulfamidase on pathology in a murine model of MPS IIIA," Exp Neurol (2011) 230(1):123-130.

Thorpe et al., "Modification of the carbohydrate in ricin with metaperiodate-cyanoborohydride mixtures. Effects on toxicity and in vivo distribution," Eur J Biochem (1985) 147(1):197-206.

Urayama et al., "Mannose 6-phosphate receptor-mediated transport of sulfamidase across the blood-brain barrier in the newborn mouse," Mol Ther (2008) 16(7):1261-1266.

Wang et al., "Instability, stabilization, and formulation of liquid protein pharmaceuticals," Int J Pharm (1999) 185(2):129-188.

Houba et al., "Improved Characteristics of a Human β-Glucuronidase Antibody Conjugate after Deglycosylation for Use in Antibody-Directed Enzyme Prodrug Therapy," Bioconjugate Chem. (1996) 7:606-611.

Meng et al., "Systemic Administration of Tripeptidyl Peptidase I in a Mouse Model of Late Infantile Neuronal Ceroid Lipofuscinosis: Effect of Glycan Modification," PLoS ONE (2012) 7(7):e40509, 7 pages.

Thorpe et al., "Modification of the carbohydrate in ricin with metaperiodate-cyanoborohydride mixtures," Eur. J. Biochem. (1985) 147:197-206.

Urayama, "Towards the successful delivery of lysosomal enzymes across the blood-brain barrier," Clinical and Experimental Neuroimmunology (2013) 4:228-238.

Zhou et al., "Brain-penetrating IgG-Iduronate 2-Sulfatase fusion protein for the mouse," Drug Metab Dispos (2012) 40(2):329-335.

* cited by examiner

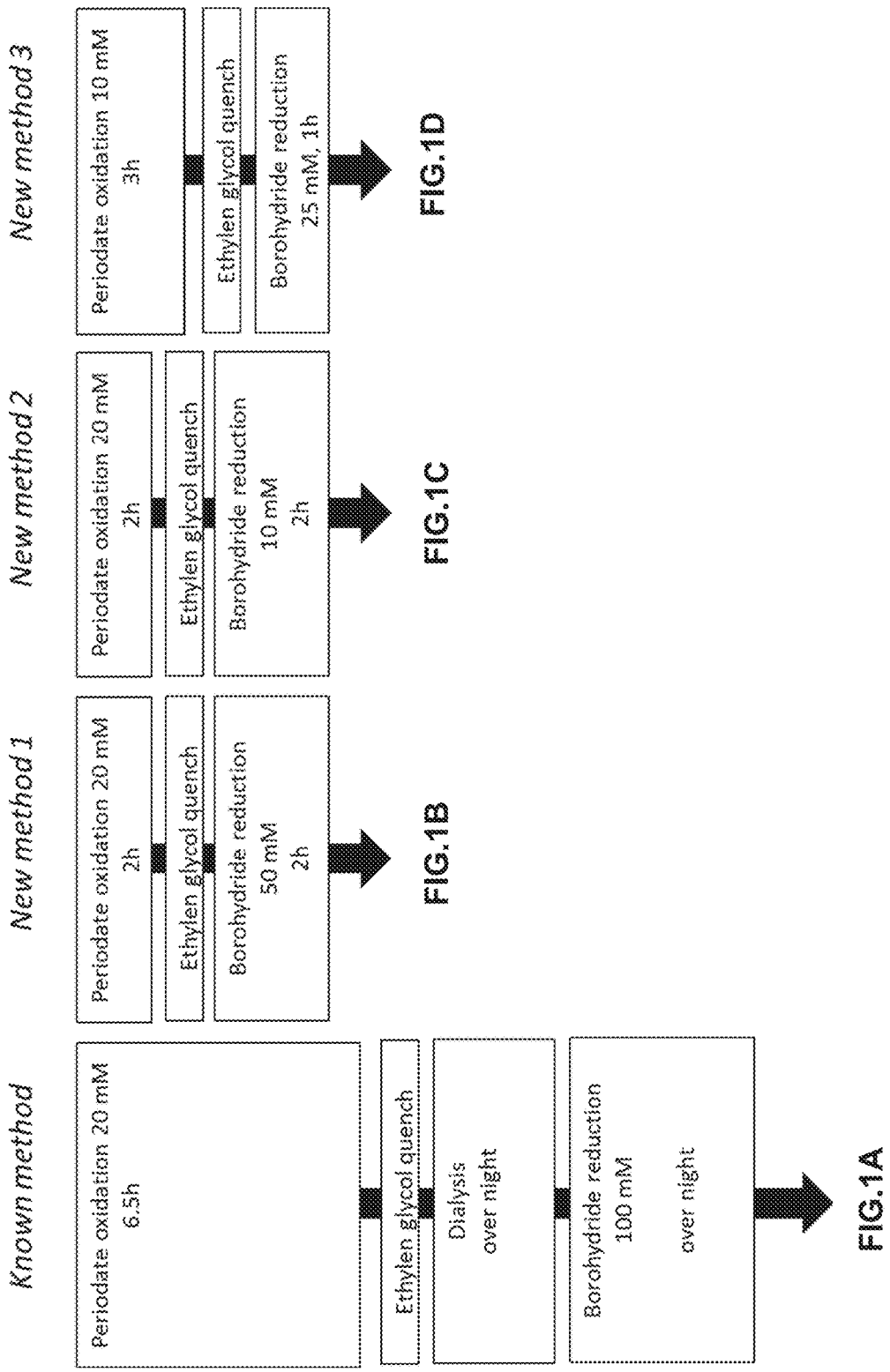

*Known method*

*New method 1*

| SEQ ID NO: | Amino acid sequence | Name |
|---|---|---|
| 1 | RPRNALLLLADDGGFESGAYNNSAIATPHLDALARRSLLFRNAFTSVSSCSPSRASLLTGLPQHQNG MYGLHQDVHHFNSFDKVRSLPLLLSQAGVRTGIIGKKHVGPETVYPFDFAYTEENGSVLQVGRNITRI KLLVRKFLQTQDDRPFFLYVAFHDPHRCGHSOPQYGTFCEKFGNGESGMGRIPDWTPQAYDPLDV LVPYFVPNTPAARADLAAQYTTVGRMDQGVGLVLQELRDAGVLNDTLVIFTSDNGIPFPSGRTNLYW PGTAEPLLVSSPEHPKRWGQVSEAYVSLLDLTPTILDWFSIPYPSYAIFGSKTIHLTGRSLLPALEAEP LWATVFGSQSHHEVTMSYPMRSVQHRHFRLVHNLNFKMPFFPIDQDFYVSPTFQDLLNRTTAGQPTG WYKDLRHYYYRARWELYDRSRDPHETQNLATDPRFAQLLEMLRDQLAKWQWETHDPWVCAPDGV LEEKLSPQCQPLHNEL | PBV2351 |
| 2 | GSRPRNALLLLADDGGFESGAYNNSAIATPHLDALARRSLLFRNAFTSVSSCSPSRASLLTGLPQHQ NGMYGLHQDVHHFNSFDKVRSLPLLLSQAGVRTGIIGKKHVGPETVYPFDFAYTEENGSVLQVGRNI TRIKLLVRKFLQTQDDRPFFLYVAFHDPHRCGHSOPQYGTFCEKFGNGESGMGRIPDWTPQAYDPL DVLVPYFVPNTPAARADLAAQYTTVGRMDQGVGLVLQELRDAGVLNDTLVIFTSDNGIPFPSGRTNL YWPGTAEPLLVSSPEHPKRWGQVSEAYVSLLDLTPTILDWFSIPYPSYAIFGSKTIHLTGRSLLPALEA EPLWATVFGSQSHHEVTMSYPMRSVQHRHFRLVHNLNFKMPFFPIDQDFYVSPTFQDLLNRTTAGQP TGWYKDLRHYYYRARWELYDRSRDPHETQNLATDPRFAQLLEMLRDQLAKWQWETHDPWVCAPD GVLEEKLSPQCQPLHNELGS | pBV1968 |
| 3 | RPRNALLLLADDGGFESGAYNNSAIATPHLDALARRSLLFRNAFTSVSSCSPSRASLLTGLPQHQNG MYGLHQDVHHFNSFDKVRSLPLLLSQAGVRTGIIGKKHVGPETVYPFDFAYTEENGSVLQVGRNITRI KLLVRKFLQTQDDRPFFLYVAFHDPHRCGHSOPQYGTFCEKFGNGESGMGRIPDWTPQAYDPLDV LVPYFVPNTPAARADLAAQYTTVGRMDQGVGLVLQELRDAGVLNDTLVIFTSDNGIPFPSGRTNLYW PGTAEPLLVSSPEHPKRWGQVSEAYVSLLDLTPTILDWFSIPYPSYAIFGSKTIHLTGRSLLPALEAEP LWATVFGSQSHHEVTMSYPMRSVQHRHFRLVHNLNFKMPFFPIDQDFYVSPTFQDLLNRTTAGQPTG WYKDLRHYYYRARWELYDRSRDPHETQNLATDPRFAQLLEMLRDQLAKWQWETHDPWVCAPDGV LEEKLSPQCQPLHNELGS | pBV1803 |

Figure 11

SEQUENCE LISTING

```
<160> NUMBER OF SEQ ID NOS: 3

<210> SEQ ID NO 1
<211> LENGTH: 482
<212> TYPE: PRT
<213> ORGANISM: Homo sapiens

<400> SEQUENCE: 1

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
                20                  25                  30

Leu Ala Arg Arg Ser Leu Leu Phe Arg Asn Ala Phe Thr Ser Val Ser
            35                  40                  45

Ser Cys Ser Pro Ser Arg Ala Ser Leu Leu Thr Gly Leu Pro Gln His
    50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Leu Ser Gln Ala Gly Val
                85                  90                  95

Arg Thr Gly Ile Ile Gly Lys Lys His Val Gly Pro Glu Thr Val Tyr
            100                 105                 110

Pro Phe Asp Phe Ala Tyr Thr Glu Glu Asn Gly Ser Val Leu Gln Val
        115                 120                 125

Gly Arg Asn Ile Thr Arg Ile Lys Leu Leu Val Arg Lys Phe Leu Gln
    130                 135                 140

Thr Gln Asp Asp Arg Pro Phe Phe Leu Tyr Val Ala Phe His Asp Pro
145                 150                 155                 160
```

His Arg Cys Gly His Ser Gln Pro Gln Tyr Gly Thr Phe Cys Glu Lys
            165                 170                 175

Phe Gly Asn Gly Glu Ser Gly Met Gly Arg Ile Pro Asp Trp Thr Pro
            180                 185                 190

Gln Ala Tyr Asp Pro Leu Asp Val Leu Val Pro Tyr Phe Val Pro Asn
            195                 200                 205

Thr Pro Ala Ala Arg Ala Asp Leu Ala Ala Gln Tyr Thr Thr Val Gly
            210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
            245                 250                 255

Pro Phe Pro Ser Gly Arg Thr Asn Leu Tyr Trp Pro Gly Thr Ala Glu
            260                 265                 270

Pro Leu Leu Val Ser Ser Pro Glu His Pro Lys Arg Trp Gly Gln Val
            275                 280                 285

Ser Glu Ala Tyr Val Ser Leu Leu Asp Leu Thr Pro Thr Ile Leu Asp
            290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
            325                 330                 335

Leu Trp Ala Thr Val Phe Gly Ser Gln Ser His His Glu Val Thr Met
            340                 345                 350

Ser Tyr Pro Met Arg Ser Val Gln His Arg His Phe Arg Leu Val His
            355                 360                 365

Asn Leu Asn Phe Lys Met Pro Phe Pro Ile Asp Gln Asp Phe Tyr Val
            370                 375                 380

Ser Pro Thr Phe Gln Asp Leu Leu Asn Arg Thr Thr Ala Gly Gln Pro
385                 390                 395                 400

Thr Gly Trp Tyr Lys Asp Leu Arg His Tyr Tyr Arg Ala Arg Trp
            405                 410                 415

Glu Leu Tyr Asp Arg Ser Arg Asp Pro His Glu Thr Gln Asn Leu Ala
            420                 425                 430

Thr Asp Pro Arg Phe Ala Gln Leu Leu Glu Met Leu Arg Asp Gln Leu
            435                 440                 445

Ala Lys Trp Gln Trp Glu Thr His Asp Pro Trp Val Cys Ala Pro Asp
450                 455                 460

Gly Val Leu Glu Glu Lys Leu Ser Pro Gln Cys Gln Pro Leu His Asn
465                 470                 475                 480

Glu Leu

<210> SEQ ID NO 2
<211> LENGTH: 484
<212> TYPE: PRT
<213> ORGANISM: Homo sapiens

<400> SEQUENCE: 2

Gly Ser Arg Pro Arg Asn Ala Leu Leu Leu Leu Ala Asp Asp Gly Gly
1               5                   10                  15

Phe Glu Ser Gly Ala Tyr Asn Asn Ser Ala Ile Ala Thr Pro His Leu
            20                  25                  30

Asp Ala Leu Ala Arg Arg Ser Leu Leu Phe Arg Asn Ala Phe Thr Ser
            35                  40                  45

```
Val Ser Ser Cys Ser Pro Ser Arg Ala Ser Leu Leu Thr Gly Leu Pro
    50                  55                  60

Gln His Gln Asn Gly Met Tyr Gly Leu His Gln Asp Val His His Phe
65                  70                  75                  80

Asn Ser Phe Asp Lys Val Arg Ser Leu Pro Leu Leu Leu Ser Gln Ala
                85                  90                  95

Gly Val Arg Thr Gly Ile Ile Gly Lys Lys His Val Gly Pro Glu Thr
            100                 105                 110

Val Tyr Pro Phe Asp Phe Ala Tyr Thr Glu Glu Asn Gly Ser Val Leu
                115                 120                 125

Gln Val Gly Arg Asn Ile Thr Arg Ile Lys Leu Leu Val Arg Lys Phe
130                 135                 140

Leu Gln Thr Gln Asp Asp Arg Pro Phe Phe Leu Tyr Val Ala Phe His
145                 150                 155                 160

Asp Pro His Arg Cys Gly His Ser Gln Pro Gln Tyr Gly Thr Phe Cys
                165                 170                 175

Glu Lys Phe Gly Asn Gly Glu Ser Gly Met Gly Arg Ile Pro Asp Trp
                180                 185                 190

Thr Pro Gln Ala Tyr Asp Pro Leu Asp Val Leu Val Pro Tyr Phe Val
                195                 200                 205

Pro Asn Thr Pro Ala Ala Arg Ala Asp Leu Ala Ala Gln Tyr Thr Thr
210                 215                 220

Val Gly Arg Met Asp Gln Gly Val Gly Leu Val Leu Gln Glu Leu Arg
225                 230                 235                 240

Asp Ala Gly Val Leu Asn Asp Thr Leu Val Ile Phe Thr Ser Asp Asn
                245                 250                 255

Gly Ile Pro Phe Pro Ser Gly Arg Thr Asn Leu Tyr Trp Pro Gly Thr
                260                 265                 270

Ala Glu Pro Leu Leu Val Ser Ser Pro Glu His Pro Lys Arg Trp Gly
                275                 280                 285

Gln Val Ser Glu Ala Tyr Val Ser Leu Leu Asp Leu Thr Pro Thr Ile
                290                 295                 300

Leu Asp Trp Phe Ser Ile Pro Tyr Pro Ser Tyr Ala Ile Phe Gly Ser
305                 310                 315                 320

Lys Thr Ile His Leu Thr Gly Arg Ser Leu Leu Pro Ala Leu Glu Ala
                325                 330                 335

Glu Pro Leu Trp Ala Thr Val Phe Gly Ser Gln Ser His His Glu Val
                340                 345                 350

Thr Met Ser Tyr Pro Met Arg Ser Val Gln His Arg His Phe Arg Leu
                355                 360                 365

Val His Asn Leu Asn Phe Lys Met Pro Phe Pro Ile Asp Gln Asp Phe
                370                 375                 380

Tyr Val Ser Pro Thr Phe Gln Asp Leu Leu Asn Arg Thr Thr Ala Gly
385                 390                 395                 400

Gln Pro Thr Gly Trp Tyr Lys Asp Leu Arg His Tyr Tyr Tyr Arg Ala
                405                 410                 415

Arg Trp Glu Leu Tyr Asp Arg Ser Arg Asp Pro His Glu Thr Gln Asn
                420                 425                 430

Leu Ala Thr Asp Pro Arg Phe Ala Gln Leu Leu Glu Met Leu Arg Asp
                435                 440                 445

Gln Leu Ala Lys Trp Gln Trp Glu Thr His Asp Pro Trp Val Cys Ala
450                 455                 460

Pro Asp Gly Val Leu Glu Glu Lys Leu Ser Pro Gln Cys Gln Pro Leu
```

-continued

```
              465                 470                 475                 480
His Asn Glu Leu

<210> SEQ ID NO 3
<211> LENGTH: 484
<212> TYPE: PRT
<213> ORGANISM: Homo sapiens

<400> SEQUENCE: 3

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
                20                  25                  30

Leu Ala Arg Arg Ser Leu Leu Phe Arg Asn Ala Phe Thr Ser Val Ser
            35                  40                  45

Ser Cys Ser Pro Ser Arg Ala Ser Leu Leu Thr Gly Leu Pro Gln His
    50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Ser Gln Ala Gly Val
                85                  90                  95

Arg Thr Gly Ile Ile Gly Lys Lys His Val Gly Pro Glu Thr Val Tyr
                100                 105                 110

Pro Phe Asp Phe Ala Tyr Thr Glu Glu Asn Gly Ser Val Leu Gln Val
            115                 120                 125

Gly Arg Asn Ile Thr Arg Ile Lys Leu Leu Val Arg Lys Phe Leu Gln
    130                 135                 140

Thr Gln Asp Asp Arg Pro Phe Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
            180                 185                 190

Gln Ala Tyr Asp Pro Leu Asp Val Leu Val Pro Tyr Phe Val Pro Asn
    195                 200                 205

Thr Pro Ala Ala Arg Ala Asp Leu Ala Ala Gln Tyr Thr Thr Val Gly
210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255

Pro Phe Pro Ser Gly Arg Thr Asn Leu Tyr Trp Pro Gly Thr Ala Glu
            260                 265                 270

Pro Leu Leu Val Ser Ser Pro Glu His Pro Lys Arg Trp Gly Gln Val
    275                 280                 285

Ser Glu Ala Tyr Val Ser Leu Leu Asp Leu Thr Pro Thr Ile Leu Asp
290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His Glu Val Thr Met
            340                 345                 350

Ser Tyr Pro Met Arg Ser Val Gln His Arg His Phe Arg Leu Val His
```

```
                    355                 360                 365
Asn Leu Asn Phe Lys Met Pro Phe Pro Ile Asp Gln Asp Phe Tyr Val
        370                 375                 380

Ser Pro Thr Phe Gln Asp Leu Leu Asn Arg Thr Thr Ala Gly Gln Pro
385                 390                 395                 400

Thr Gly Trp Tyr Lys Asp Leu Arg His Tyr Tyr Arg Ala Arg Trp
                405                 410                 415

Glu Leu Tyr Asp Arg Ser Arg Asp Pro His Glu Thr Gln Asn Leu Ala
            420                 425                 430

Thr Asp Pro Arg Phe Ala Gln Leu Leu Glu Met Leu Arg Asp Gln Leu
            435                 440                 445

Ala Lys Trp Gln Trp Glu Thr His Asp Pro Trp Val Cys Ala Pro Asp
        450                 455                 460

Gly Val Leu Glu Glu Lys Leu Ser Pro Gln Cys Gln Pro Leu His Asn
465                 470                 475                 480

Glu Leu Gly Ser
```

MODIFIED SULFAMIDASE AND PRODUCTION THEREOF

CROSS REFERENCE TO RELATED APPLICATIONS

This application is a continuation of International Application No. PCT/EP2015/057256, filed Apr. 1, 2015 and claims priority to and the benefit of European Application No. 14162996.4, filed on Apr. 1, 2014, the entire contents each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183922000901_SeqList.txt, date recorded: Jul. 22, 2015, size: 12,867 bytes).

TECHNICAL FIELD

The present disclosure relates to a modified sulfamidase, compositions comprising a modified sulfamidase and methods for producing a modified sulfamidase. Furthermore, use of a modified sulfamidase in therapy such as in treatment of a lysosomal storage disease is disclosed.

BACKGROUND

Lysosomal Storage Disease

The lysosomal compartment functions as a catabolic machinery that degrades waste material in cells. Degradation is achieved by a number of hydrolases and transporters compartmentalized specifically to the lysosome. There are today over 40 identified inherited diseases where a link has been established between disease and mutations in genes coding for lysosomal proteins. These diseases are defined as lysosomal storage diseases (LSDs) and are characterized by a buildup of a metabolite (or metabolites) that cannot be degraded due to the insufficient degrading capacity. As a consequence of the excess lysosomal storage of the metabolite, lysosomes increase in size. How the accumulated storage material cause pathology is not fully understood but may involve mechanisms such as inhibition of autophagy and induction of cell apoptosis (Cox & Cachón-González, J Pathol 226: 241-254 (2012)).

Enzyme Replacement Therapy

Storage can be reduced by administration of a lysosomal enzyme from a heterologous source. It is well established that intravenous administration of a lysosomal enzyme results in its rapid uptake by cells via a mechanism called receptor mediated endocytosis. This endocytosis is mediated by receptors on the cell surface, and in particular the two mannose-6 phosphate receptors (M6PR) have been shown to be pivotal for uptake of certain lysosomal enzymes (Neufeld; Birth Defects Orig Artic Ser 16: 77-84 (1980)). M6PR recognize phosphorylated oligomannose glycans which are characteristic for lysosomal proteins.

Based on the principle of receptor mediated endocytosis, enzyme replacement therapies (ERT) are today available for six LSDs, (Gaucher, Fabrys, Pompe and the Mucopolysaccharidosis type I, II and VI). These therapies are efficacious in reducing lysosomal storage in various peripheral organs and thereby ameliorate some symptoms related to the pathology.

A majority of the LSDs however cause lysosomal storage in the central nervous system (CNS) and consequently present a repertoire of CNS related signs and symptoms. A major drawback with intravenously administered ERT is the poor distribution to the CNS. The CNS is protected from exposure to blood borne compounds by the blood brain barrier (BBB), formed by the CNS endothelium. The endothelial cells of the BBB exhibit tight junctions which prevent paracellular passage, show limited passive endocytosis and in addition lack some of the receptor mediated transcytotic capacity seen in other tissues. Notably, in mice M6PR mediated transport across the BBB is only observed up to two weeks after birth (Urayama et al, Mol Ther 16: 1261-1266 (2008)).

Glycosylation of Lysomal Enzymes

In general, N-glycosylations can occur at a Asn-X-Ser/Thr sequence motif. To this motif the initial core structure of the N-glycan is transferred by the glycosyltransferase oligosaccharyltransferase, within the reticular lumen. This common basis for all N-linked glycans is made up of 14 residues; 3 glucose, 9 mannose, and 2 N-acetylglucosamine. This ancestor is then converted into three general types of N-glycans; oligomannose, complex and hybrid (FIG. 7), by the actions of a multitude of enzymes that both trim down the initial core and add new sugar moieties. Each mature N-glycan contains the common core Man(Man)2-GlcNAc-GlcNAc-Asn, where Asn is the attachment point to the protein.

In addition, proteins directed to the lysosome carry one or more N-glycans which are phosphorylated. The phosphorylation occurs in the Golgi and is initiated by the addition of N-acetylglucosamine-1-phosphate to C-6 of mannose residues of oligomannose type N-glycans. The N-acetylglucosamine is cleaved off to generate Mannose-6-phosphate (M6P) residues, that are recognized by M6PRs and will initiate the transport of the lysosomal protein to the lysosome. The resulting N-glycan is then trimmed to the point where the M6P is the terminal group of the N-glycan chain. (Essentials of Glycobiology. 2nd edition. Varki A, Cummings R D, Esko J D, et al, editors. Cold Spring Harbor (N.Y.): Cold Spring Harbor Laboratory Press; 2009.)

The binding site of the M6PR requires a terminal M6P group that is complete, as both the sugar moiety and the phosphate group is involved in the binding to the receptor (Kim et al, Curr Opin Struct Biol 19(5):534-42 (2009)).

Enzyme Replacement Therapy Targeting the Brain by Glycan Modification

A potential strategy to increase distribution of lysomal enzyme to the CNS has been disclosed in WO 2008/109677. In this published application, chemical modification of β-glucuronidase using sodium meta-periodate and sodium borohydride is described (see also Grubb et al, Proc Natl Acad Sci USA 105: 2616-2621 (2008)). This modification, consisting of oxidation with 20 mM sodium periodate for 6.5 h, followed by quenching, dialysis and reduction with 100 mM sodium borohydride overnight (referred to hereinafter as known method), substantially improved CNS distribution of β-glucuronidase and resulted in clearance of neuronal storage in a murine model of the LSD mucopolysaccharidosis VII. Although the underlying mechanism of brain distribution is unclear, it was noted that the chemical modification disrupted glycan structure on β-glucuronidase and it was further demonstrated that receptor mediated endocytosis by M6PR was strongly reduced.

The chemical modification strategy has been investigated for other lysosomal enzymes. For example, modification according to the known method did not improve distribution to the brain of intravenously administrated protease tripeptidyl peptidase I (Meng et al, PLoS One (2012)). Neither has satisfactory results been demonstrated for sulfamidase. Sulfamidase, chemically modified according to the known method, did indeed display an increased half-life in mice but no effect in the brain of MPS IIIA mice. The chemically modified sulfamidase did not distribute to the brain parenchyma when given repeatedly by intravenous administration (Rozaklis et al, Exp Neurol 230: 123-130 (2011)).

Thus, there are still no effective ERT for treatment of LSDs with neurological engagement, such as MPS IIIA. Novel sulfamidase compounds that can be transported across the BBB while remaining enzymatically active would be of great value in the development of systemically administrated compounds for enzyme replacement therapies for the treatment of LSDs with CNS related pathology, such as MPS IIIA.

DISCLOSURE OF THE INVENTION

It is an object of the present invention to provide novel sulfamidase compounds allowing development of an enzyme replacement therapy for LSDs such as MPS IIIA.

It is another object of the present invention to provide a novel sulfamidase compound that may be transported across the blood brain barrier in mammals and which may exhibit an enzymatic (catalytic) activity in the brain of said mammal.

Yet another object of the present invention is to provide a novel sulfamidase compound exhibiting improved stability.

These and other objects, which will be apparent to a skilled person from the present disclosure, are achieved by the different aspects of the invention as defined in the appended claims and as generally disclosed herein.

There is, in one aspect of the invention, provided a modified sulfamidase comprising substantially no epitopes for glycan recognition receptors, thereby enabling transportation of said sulfamidase across the blood brain barrier of a mammal, wherein said sulfamidase has catalytic activity in the brain of said mammal.

The modified sulfamidase according to the invention is thus modified in that epitopes for glycan recognition receptors have been removed, for example as compared to an unmodified sulfamidase (SEQ ID NO:1). As has been demonstrated by the applicant for example in the appended examples, such a modified sulfamidase is less prone to cellular uptake which is a consequence of removal of epitopes for glycan recognition receptors such as the two mannose-6 phosphate receptors (M6PR) (see Examples 6 and 7). The almost complete absence of said epitopes reduces the affinity of the modified sulfamidase with respect to glycan recognition receptors. In particular, this might reduce the receptor mediated endocytosis of the modified sulfamidase in peripheral tissue, which in turn may result in a reduced clearance of modified sulfamidase from plasma when e.g. administrated intravenously to a mammal. This is probably at least partly due to the inhibition of receptor mediated uptake in peripheral tissue following chemical modification of sulfamidase (as demonstrated in the cellular uptake studies of Example 6). From a dosing perspective, reduced clearance of modified sulfamidase may advantageously allow for development of long-acting medicaments that can be administered to patients less frequently.

By glycan recognition receptors is meant receptors that recognize and bind proteins mainly via glycan moieties of the proteins. Such receptors can, in addition to the mannose 6-phosphate receptors, be exemplified by the mannose receptor; which selectively binds proteins where glycans exhibit exposed terminal mannose residues. Lectins constitute another large family of glycan recognition receptors which can be exemplified by the terminal galactose recognizing asialoglycoprotein receptor 1 recognizing terminal galactose residues on glycans. Epitopes for glycan recognition receptors can thus be understood as (part of) glycan moieties recognized by such receptors.

In this context, a modified sulfamidase comprising substantially no epitopes for glycan recognition receptors should preferably be understood as a modified sulfamidase comprising nearly no epitopes for glycan recognition receptors, or only minor amounts of such epitopes. In preferred embodiments, the modified sulfamidase comprises no (detectable) epitopes for glycan recognition receptors. In particular, the modified sulfamidase comprises no (detectable) mannose-6-phosphate moieties, mannose moieties, or galactose moieties that constitute epitopes for the endocytic M6PR type 1 and 2, the mannose receptor and the galactose receptor, respectively. In one embodiment, said epitopes may thus be recognized by at least one glycan recognition receptor selected from M6PR type 1 and 2, mannose receptor and galactose receptor. In particular, said at least one glycan recognition receptor may be selected from M6PR type 1 and 2. In correspondence with what is defined above, said epitopes, which are found on natural glycan moieties, represent at least one type of moiety selected from a mannose-6-phosphate moiety, a mannose moiety and a galactose moiety. In particular embodiments, these are absent from the modified sulfamidase as disclosed herein.

Moreover, the modified sulfamidase according to aspects described herein not only distributes to the brain of a mammal, but it also displays (retained) enzymatic activity or catalytic activity in the brain of said mammal. The enzymatic activity of the modified sulfamidase is retained at least partly from an unmodified form of the sulfamidase. The enzymatic activity is moreover retained as compared to a sulfamidase modified according to prior art methods which displays no (distribution nor) enzymatic activity in the brain of mice. Thus, the modified sulfamidase as disclosed herein may affect lysosomal storage in the brain of mammals, such as to decrease lysosomal storage, for example lysosomal storage of hexosamine N-sulfate [α-1,4] uronic acid (HNS-UA) as demonstrated e.g. in Example 8. The retained catalytic activity may for instance depend on level of preservation versus modification of a catalytic amino acid residue at the active site of sulfamidase.

Sulfamidase belongs to the protein family of sulfatases. Sulfatases are a family of proteins of common evolutionary origin that catalyze the hydrolysis of sulfate ester bonds from a variety of substrates. Thus, "catalytic activity" of modified sulfamidase as used herein may refer to hydrolysis of sulfate ester bonds, preferably in lysosomes of peripheral tissue and/or in lysosomes in the brain of a mammal Catalytic activity of modified sulfamidase may thus result in reduction of lysosomal storage, such as heparan sulfate storage, in the brain of a mammal suffering from a lysosomal storage disease. Catalytic activity may for example be measured in an animal model, for example as outlined in Example 8.

Sulfatases share a common fold with a central β-sheet which consists of 10 β-strands. The active site of sulfamidase is located at the end of the central β-sheet and contains a conserved cysteine in position 50 of SEQ ID NO:1 that is post-translationally modified to a Cα-formylglycine (FGly). This reaction takes place in the endoplasmic reticulum by the FGly generating enzyme. This FGly residue in position 50 (FGly50) is directly involved in the hydrolysis of sulfate ester bonds and the modification seems necessary for the enzymes to be active. Notably, mutation of the conserved cysteine to a serine (Ser) in arylsulfatase A and B prevents FGly formation and yields inactive enzymes (Recksiek et al, J Biol Chem 13; 273(11):6096-103 (1998)). When preservation of active site is discussed herein, it should primarily be understood as preservation of the post-translational FGly50 of SEQ ID NO:1. Thus, in such instances the modified sulfamidase should be understood as comprising a polypeptide consisting of an amino acid sequence as defined in SEQ ID NO:1 or an amino acid sequence having a sequence identity as defined below with such an amino acid sequence.

In one embodiment, said active site comprises a catalytic residue in a position corresponding to position 50 of SEQ ID NO:1 providing said catalytic activity. This catalytic residue is in a further embodiment FGly50.

In one embodiment, the modified sulfamidase has a relative content of natural glycan moieties of around 25% of the content of natural glycan moieties in unmodified recombinant sulfamidase. Said epitopes for glycan recognition receptors may thus be found on natural glycan moieties, and such natural glycan moieties are thus substantially absent in the modified sulfamidase as described herein. The relative content of natural glycan moieties in modified sulfamidase may in preferred embodiments be less than 25%, such as less than 20%, such as less than 15%, such as less than 10%, such as less than 5%. In a particular embodiment, the content of natural glycan moieties is less than 1%. The relative content of glycan moieties can be understood as the content of remaining intact natural glycan moieties after modification of sulfamidase. As demonstrated in the appended Examples, relative quantification of glycopeptides may be based on LC-MS and peak areas from reconstructed ion chromatograms. Alternative quantification methods are known to the person skilled in the art. A relative content of natural glycans at a level of less than 25% may advantageously reduce receptor mediated endocytosis of sulfamidase into cells via glycan recognition receptors, and improve transportation across the blood brain barrier. A relative content of natural glycans at a level of 25% may be represented, as further exemplified below, by one natural glycan. Natural glycan moieties should in this respect be understood as glycan moieties naturally occurring in sulfamidase that are post-translationally modified in the endoplasmatic reticulum and golgi compartments of eukaryotic cells.

In one embodiment, said natural glycan moieties are disrupted by single bond breaks and double bond breaks in said modified sulfamidase, wherein glycan disruption by single bond break is predominant. In particular, natural glycan moieties of said sulfamidase are disrupted by single bond breaks and double bond breaks, wherein the extent of single bond breaks is at least 60% in oligomannose glycans. In particular embodiments, the extent of single bond breaks is at least 65%, such as at least 70%, such as at least 75%, such as at least 80%, such as at least 82%, such as at least 85% in the oligomannose type of glycans. The extent of single bond breaks vs double bond breaks may be measured as described in Examples 10 and 11. As described in other aspects herein, sulfamidase may be modified by reaction with periodate such as to disrupt the structure of the glycan moieties naturally occurring on sulfamidase. The remaining glycan structure of the modified sulfamidase may have been at least partially disrupted in that at least one periodate catalyzed cleavage, i.e. at least one single bond break, has occurred in each of the naturally occurring glycan moieties. The "modification" of said modified sulfamidase is, in comparison with a unmodified sulfamidase, at least partly represented by said disruption of natural glycan moieties.

In one embodiment, the modified sulfamidase comprises a polypeptide consisting of an amino acid sequence as defined in SEQ ID NO:1, or a polypeptide having at least 95% sequence identity with an amino acid sequence as defined in SEQ ID NO:1. In a non-limiting example, said polypeptide has at least 90% sequence identity with an amino acid sequence as defined in SEQ ID NO:1, such as at least 95% sequence identity with an amino acid sequence as defined in SEQ ID NO:1, such as at least 98% sequence identity with an amino acid sequence as defined in SEQ ID NO:1. The modified sulfamidase according to the invention may thus comprise a polypeptide having an amino acid sequence which is highly similar to SEQ ID NO:1. Said polypeptide may however for example be extended by one or more C- and/or N-terminal amino acid(s), making the actual modified sulfamidase sequence longer than the sequence of SEQ ID NO:1. Similarly, in other instances the modified sulfamidase may have an amino acid sequence which is shorter than the amino acid sequence of SEQ ID NO:1, the difference in length e.g. being due to deletion(s) of amino acid residue(s) in certain position(s) of the sequence.

In one embodiment, said epitopes are absent at at least four of the five N-glycosylation sites: asparagine (N) in position 21 (N(21)), N in position 122 (N(122)), N in position 131 (N(131)), N in position 244 (N(244)), and N in position 393 (N(393)) of SEQ ID NO:1. Alternatively formulated, said modified sulfamidase comprises natural glycan moieties at no more than one of said N-glycosylation sites. In certain embodiments, said modified sulfamidase comprises natural glycan moieties at one of said N-glycosylation sites; said N-glycosylation site optionally being N(131). Alternatively, said epitopes, or glycan moieties, are absent at N(21), N(122), N(244), and N(393) of said modified sulfamidase polypeptide. Advantages of such a modified sulfamidase lacking glycan moieties at the identified sites are as accounted for above; i.e. the cellular uptake might be further reduced and the transportation across the blood brain barrier might be further facilitated.

In one embodiment, said natural glycan moieties of said sulfamidase correspond to N-glycosylation at N in position 21 (N(21)), N in position 131 (N(131)), N in position 244 (N(244)), and N in position 393 (N(393)) of SEQ ID NO:1. Thus, unmodified sulfamidase may be naturally glycosylated at these four sites. In this embodiment, the modified sulfamidase thus may have relative content of natural glycan moieties in these positions being around, or less than, 25% of the content of glycan moieties in corresponding positions of unmodified recombinant sulfamidase. In one particular embodiment of the modified sulfamidase, at least three of the four naturally occurring glycosylation sites identified above lack epitopes for glycan recognition receptors.

As mentioned above, the glycan moiety at the N-glycosylation site N(131) of sulfamidase is a glycan moiety naturally occurring on unmodified recombinant sulfamidase. N(131) is the glycosylation site on sulfamidase that, once glycosylated, is considered to cause a major part of the receptor mediated uptake in peripheral tissues as compared to the other glycosylation sites. The disruption of the glycan moiety naturally occurring on N(131), which is of oligomannose type, may thus influence clearance of modified sulfamidase from plasma. The disruption of said N(131) oligomannose may be characterized by an extent of at least 60% single bond breaks. Thus, disruption by single bond breaks is more frequent than disruption by double bond breaks.

In one embodiment, said epitopes are absent at all of said five N-glycosylation sites of the modified sulfamidase. Glycan moieties are thus absent at all five N-glycosylation sites: N in position 21 (N(21)), N in position 122 (N(122)), N in position 131 (N(131)), N in position 244 (N(244)), and N in position 393 (N(393)) of SEQ ID NO:1. A modified sulfamidase lacking glycan moieties in these five sites may improve the modified enzyme's pharmacokinetics further, for example in that the plasma clearance in a mammal may be further reduced. As a consequence, dosing frequency of a modified sulfamidase may hence also be further reduced.

Human sulfamidase (EC 3.10.1.1; SEQ ID NO:1) is encoded by the SGSH gene. Sulfamidase is also known under the names sulphamidase, N-sulphoglucosamine sulphohydrolase, N-sulfoglucosamine sulfohydrolase, sulphamate sulphohydrolase, heparan sulfate sulfatase, heparin sulfamidase, 2-desoxy-D-glucoside-2-sulphamate sulphohydrolase, and N-sulfo-D-glucosamine sulfohydrolase, and the term "sulfamidase" as used herein should be understood as equivalent to these alternative names.

In one embodiment, said modified sulfamidase is isolated.

In one embodiment, said sulfamidase is human sulfamidase.

In one embodiment, said sulfamidase prior to modification is glycosylated.

In one embodiment, said modified sulfamidase is recombinant. Sulfamidase may be produced recombinantly for example as described in Example 1 herein. Sulfamidase may be produced in eukaryotic cells, exemplified by, but not limited to, Chinese ovary hamster (CHO) cells, human embryonic kidney cells, or lymphoid cell lines of murine origin. In addition, sulfamidase may be produced in insect cells, plant cells, or yeast cells. Recombinant human sulfamidase is known from e.g. patent Nos. U.S. Pat. No. 5,863,782; U.S. Pat. No. 5,972,333; U.S. Pat. No. 6,200,563; U.S. Pat. No. 6,458,579; and U.S. Pat. No. 6,491,913. It should be understood that for the purposes of the present invention, human sulfamidase may be produced as described in any of the cited US patents, which are hereby incorporated by reference.

In one embodiment, said modified sulfamidase comprises a polypeptide consisting of an amino acid sequence as defined in SEQ ID NO:1, or a polypeptide having at least 95% sequence identity with a polypeptide as defined in SEQ ID NO:1, wherein glycan moieties are absent at at least four of the five N-glycosylation sites: N in position 21 (N(21)), N in position 122 (N(122)), N in position 131 (N(131)), N in position 244 (N(244)), and N in position 393 (N(393)) of SEQ ID NO:1, and said sulfamidase optionally has an intact c-terminal. In one embodiment thereof, the c-terminal part represented by amino acids 436-484 of SEQ ID NO:1 is intact.

In one aspect, there is provided a sulfamidase composition, comprising modified sulfamidase having substantially no epitopes for glycan recognition receptors, thereby enabling transportation of said sulfamidase across the blood brain barrier of a mammal, and a Cα-formylglycine (FGly) to serine (Ser) ratio at the active site that is greater than 1, thereby providing catalytic activity in the brain of a mammal. For example, said modified sulfamidase comprises a polypeptide consisting of an amino acid sequence as defined in SEQ ID NO:1, or a polypeptide having at least 95% sequence identity with a polypeptide as defined in SEQ ID NO:1. In such examples, the FGly to Ser ratio may be referred to as a FGly50 to Ser50 ratio. The defined ratio thus implies that the FGly50 is present to a larger extent than Ser50. Preferably, the ratio is larger than 1.5, more preferably larger than 2.3, more preferably larger than 4, and most preferably the ratio is around 9. A larger ratio indicates that the catalytic activity of the modified sulfamidase to a larger extent may be retained from an unmodified form of sulfamidase.

The advantages of a composition comprising a modified sulfamidase are similar to the advantages of a modified sulfamidase as such. Thus, a composition comprising modified sulfamidase may exhibit an improved half-life in plasma compared to an unmodified sulfamidase or a composition comprising unmodified sulfamidase. In addition, said modified sulfamidase may exhibit improved distribution to the brain of a mammal, as well as a retained catalytic activity in the brain, compared for example to an unmodified sulfamidase.

In one embodiment, the sulfamidase composition has a relative content of natural glycan moieties being around 25% of the content of natural glycan moieties in unmodified recombinant sulfamidase. Said epitopes for glycan recognition receptors may thus be found on natural glycan moieties, and such natural glycan moieties are thus substantially absent in the sulfamidase composition as described herein. A composition of modified sulfamidase wherein the relative content of natural glycan moieties of the composition as such is around 25% may for example be represented by a composition of modified sulfamidase wherein each sulfamidase comprises one natural glycan, for example one natural glycan moiety at one of the previously mentioned N-glycosylation sites. The relative content of natural glycan epitopes in the sulfamidase composition may in preferred embodiments be less than 20%, less than 15%, less than 10%, less than 5%. In some instances, the relative content of natural glycan moieties is less than 4%, 3%, 2%, 1%, 0.5%, such as less than 0.1%, such as less than 0.01%. A composition of sulfamidase having a relative content of natural glycan moieties at these levels is a composition wherein only trace amounts of natural glycan moieties can be found. Thus, the composition is a mixture of modified sulfamidases in which the natural glycan moieties are more or less disrupted. In a particular embodiment, the content of natural glycan moieties is less than 1%. A relative content of natural glycans at a level of around or less than 25% may advantageously reduce receptor mediated endocytosis of sulfamidase into cells via glycan recognition receptors, and improve transportation across the blood brain barrier.

In one particular embodiment of the composition aspect, said epitopes are absent at at least four of the five N-glycosylation sites: asparagine (N) in position 21 (N(21)), N in position 122 (N(122)), N in position 131 (N(131)), N in position 244 (N(244)), and N in position 393 (N(393)) of SEQ ID NO:1, preferably said epitopes are absent at N(21), N(122), N(244) and N(393). Alternatively formulated, said modified sulfamidase of the composition comprises natural glycan moieties at no more than one of said N-glycosylation sites, said N-glycosylation site optionally being N(131).

In one embodiment of the composition aspect, no more than 5% (by weight) of said modified sulfamidase is present in multimeric forms having a molecular weight of above $10^{10}$ kDa.

In one embodiment of the composition aspect, no more than 5% (by weight) of said modified sulfamidase is present in oligomeric forms, said oligomeric forms having a molecular weight of between 180 and 480 kDa. The presence of oligomeric, multimeric, or aggregated forms, can for example be determined by dynamic light scattering or by size exclusion chromatography. In this context, aggregated forms should be understood as high molecular weight protein forms composed of structures ranging from natively folded to unfolded monomers. Aggregated forms of a protein can enhance immune response to the monomeric form of the protein. The most likely explanation for an enhanced immune response is that the multivalent presentations of antigen cross link B-cell receptors and thus induce an immune response. This is a phenomenon which has been utilized in vaccine production where the antigen is presented to the host in an aggregated form to ensure a high immune response. For therapeutic proteins the dogma is the opposite; any content of high molecular weight forms should be minimized or avoided in order to minimize the immune response (Rosenberg, AAPS J, 8:E501-7 (2006)). Thus, reduction of oligomeric, multimeric and/or aggregate forms may thus provide an enzyme more suitable for use in therapy.

Another aspect of aggregation is that occurrence of even a small amount in a sample may induce aggregation of normally folded proteins. The aggregated material generally has no or low remaining activity and poor solubility. The appearance of aggregates can be one of the factors that determine the shelf-life of a biological medicine (Wang, Int J Pharm, 185:129-88 (1999)).

The term "composition" as used herein should be understood as encompassing solid and liquid forms. A composition may preferably be a pharmaceutical composition, suitable for administration to a patient (e.g. a mammal) for example by injection or orally.

It should moreover be understood that the embodiments, and their advantages, disclosed in relation to the modified sulfamidase aspects are embodiments also of the composition aspect. In the same way, the embodiments of the composition aspect should also be regarded as embodiments of the modified sulfamidase aspects, where applicable.

In one embodiment, said modified sulfamidase or said sulfamidase composition is for use in therapy.

In one embodiment, said mammalian brain is the brain of a human being. In a related embodiment, said mammal is thus a human.

In one embodiment, said mammalian brain is the brain of a mouse. In a related embodiment, said mammal is thus a mouse.

In one embodiment, said modified sulfamidase or sulfamidase composition is for use in treatment of a mammal afflicted with a lysomal storage disease, in particular mucopolysaccharidosis IIIA (MPS IIIA).

In one embodiment, said modified sulfamidase or sulfamidase composition for use reduces heparan sulfate storage in the brain of said mammal. In particular, said heparan sulfate storage is reduced by at least 30% in e.g. an animal model, such as at least 35%, at least 40%, or at least 50%.

In one aspect, there is provided a modified sulfamidase, wherein said sulfamidase has been prepared by sequential reaction with an alkali metal periodate and an alkali metal borohydride, thereby modifying epitopes for glycan recognition receptors of the sulfamidase and reducing the activity of the sulfamidase with respect to said glycan recognition receptors, while retaining catalytic activity of said sulfamidase. The sulfamidase is thus modified in that its epitopes, or glycan moieties, present in its natural, glycosylated form prior to modification has been essentially inactivated by said modification. The presence of epitopes for glycan recognition receptors have thus been reduced in the modified sulfamidase. It should be understood that the embodiments, and their advantages, disclosed in relation to the other aspects disclosed herein, such as the aspects related to modified sulfamidase, composition and method of preparation, are embodiments also of this aspect. In particular, the various method embodiments disclosed below provide further exemplary definition of the preparation of said modified sulfamidase in terms of specific reaction conditions. Similarly, the embodiments disclosed in relation to the modified sulfamidase and composition aspects above provide further exemplary definition of the modified sulfamidase.

There is, in one aspect, provided a method of preparing a modified sulfamidase, said method comprising: a) reacting a glycosylated sulfamidase with an alkali metal periodate, and b) reacting said sulfamidase with an alkali metal borohydride for a time period of no more than 2 h; thereby modifying glycan moieties of the sulfamidase and reducing the activity of the sulfamidase with respect to glycan recognition receptors, while retaining catalytic activity of said sulfamidase. Said borohydride is optionally used at a concentration of between 10 and 80 mM, such as at a concentration of between 10 and 80 mM.

The above method thus provides mild chemical modification of sulfamidase that reduces the presence of epitopes for glycan recognition receptors, said epitopes for example being represented by natural glycan moieties as described herein. This advantageously may provide a modified sulfamidase suitable for targeting the brain of a mammal. The mild method moreover modifies said epitopes without substantially altering the catalytic activity of the sulfamidase. In particular, catalytic activity may be retained by retaining FGly50 at the active site of sulfamidase. Thus, while improving distribution properties of the enzyme, the method does not eliminate catalytic activity. Further advantages with the modified sulfamidase prepared by the mild method are as accounted for above, e.g. for the sulfamidase and composition aspects.

The method allows for glycan modification by periodate cleavage of carbon bonds between two adjacent hydroxyl groups of the glycan (carbohydrate) moieties. In general, periodate oxidative cleavage occurs where there are vicinal diols present. The diols have to be present in an equatorial—equatorial or axial—equatorial position. If the diols are present in a rigid axial-axial position no reaction takes place (Kristiansen et al, Car. Res (2010)). The periodate treatment will break the bond between C2 and C3 and/or C3 and C4 of the M6P moiety, thus yielding a structure that is incapable of binding to a M6P-receptor. In general, other terminal hexoses will also be processed in a similar way. Non-terminal 1-4 linked residues are cleaved between C2 and C3 only, whereas non-terminal (1-3) linked residues are resistant to cleavage. In FIG. 7 the points of possible modification are marked with an asterisk in the three general types of N-glycans; oligomannose, complex and hybrid. As further demonstrated in appended FIGS. 8-10, the method as disclosed herein provides a modified sulfamidase wherein the natural glycan moieties have been disrupted by a limited number of bond breaks as compared to sulfamidase modified according to previously known methods. The presently disclosed method predominantly results in a single-type of bond breaks in sugar moieties of the glycan moieties of sulfamidase (see FIGS. 8A and 8B). The partial glycan oxidation with preferentially single bond breaks in sugar moieties of the glycan moities is a characteristic of the relatively mild chemical modification methods described herein. In order to achieve sulfamidase with partial glycan oxidation and predominantly single bond breaks in sugar moieties of the glycan moieties, conditions as described below and as exemplified in Example 4 can be used.

The method of preparing a modified sulfamidase, and the modified sulfamidase as described herein, are improved over prior art methods and compounds. Primarily, the inventors have surprisingly found that the novel modified sulfamidase is distributed to and displays catalytic activity in the mammalian brain. Examples 3 and 5 moreover provide comparisons between prior art methods and sulfamidases and the methods and sulfamidases as disclosed herein. The results in these examples show that sulfamidase modified according to known methods contains amino acid residues modifications, and displays polypeptide chain cleavages and protein aggregation. Of particular interest is the observed conversion of the catalytic FGly residue to a Ser residue at the active site in the sulfamidase modified according to the previous method. The relatively short duration of the reduction step in the novel method seems to positively influence the catalytic activity of the modified enzyme.

In one embodiment of the method aspect, said glycosylated sulfamidase polypeptide comprises glycan moieties at at least four asparagine residues (N glycosylation sites).

In one embodiment of the method aspect, said glycosylated asparagines residues are: N in position 21 (N(21)), N in position 131 (N(131)), N in position 244 (N(244)), and N in position 393 (N(393)) of SEQ ID NO:1. These N-glycosylation sites thus correspond to natural glycan moieties.

In one embodiment of the method aspect, said alkali metal periodate oxidizes cis-glycol groups of the glycan moieties to aldehyde groups.

In one embodiment of the method aspect, said alkali metal borohydride reduces said aldehydes to alcohols.

In one embodiment of the method aspect, step a) and step b) are performed in sequence without performing an intermediate step. The inventors have found that step b) may be performed immediately after step a), or after an optional quenching step a2) as described below, thereby omitting an intermediate step for removal of reactive reagents by e.g. dialysis, ultrafiltration, precipitation or buffer change and thus avoiding long exposure of sulfamidase to reactive aldehyde intermediates. Proceeding with step b) after step a), or optionally a2), the overall reaction duration is also advantageously reduced.

In the following paragraphs, specific embodiments for step a) is disclosed. It should be understood that unless defined otherwise specific embodiments of aspects disclosed herein can be combined.

In one embodiment, said alkali metal periodate is sodium meta-periodate.

In one embodiment, said reaction of step a) is performed for a time period of no more than 4 h, such as no more than 3 h, such as no more than 2 h, such as no more than 1 h, such as around 0.5 h. In certain embodiments, the reaction of step a) is performed for at least 0.5 h. The reaction preferably has a duration of around 3 h, 2 h, 1 h, or less than 1 h. The inventors have found that a duration of step a) of no more than 4 hours efficiently inactivates epitopes for glycan recognition receptors. In addition, a duration of no more than 4 h still gives rise to a less degree of strand-breaks of the polypeptide chain compared to the degree of strand-breaks observed for sulfamidase produced according to known methods. This has been demonstrated by the inventors for example in Example 4 and 5.

In one embodiment, said periodate is used at a (final) concentration of no more than 20 mM, such as no more than 15 mM, such as around 10 mM. The periodate may be used at a concentration of 8-20 mM, preferably around 10 mM. Alternatively, the periodate is used at a concentration of less than 20 mM, such as between 10 and 19 mM. Lower concentration of alkali metal periodate, such as sodium meta-periodate, has been found to reduce the degree of strand-breaks of the polypeptide chain, as well as associated oxidation on amino acids side-chains, such as oxidation of the methionine residue in position 226 of SEQ ID NO:1 (Met226).

In one embodiment, said reaction of step a) is performed at ambient temperature, and preferably at a temperature of between 0 and 22° C. In a preferred embodiment, the reaction of said step a) is performed at a temperature of 0-8° C., such as at a temperature of 0-4° C. In a preferred embodiment, the reaction of step a) is performed at a temperature of around 8° C., at a temperature of around 4° C. or at a temperature of around 0° C.

In one embodiment, said reaction of step a) is performed at a pH of 3 to 7. This pH should be understood as the pH at the initiation of the reaction. In particular embodiments, the pH used in step a) is 3-6, such as 4-5. In specific embodiments, the pH used in step a) is around 6, around 5, or around 4. By lowering the pH of step a), the concentration of periodate or the reaction time of step a) may be reduced.

In one embodiment, said periodate is sodium meta-periodate and is used at a (final) concentration of no more than 20 mM, such as no more than 15 mM, such as around 10 mM. In one embodiment, said sodium meta-periodate is used at a concentration of 8-20 mM. In preferred embodiments, sodium meta-periodate is used at a concentration of around 10 mM.

In one embodiment, said periodate is sodium meta-periodate and is used at a (final) concentration of no more than 20 mM, such as no more than 15 mM, such as around 10 mM, and said reaction of step a) is performed for a time period of no more than 4 h, such as no more than 3 h, such as no more than 2 h, such as no more than 1 h, such as around 0.5 h. Thus, compared to prior art methods, a concentration of 20 mM periodate and a reaction duration of no more than 4 h may result in less strand-break and oxidation. Decreasing the periodate concentration further while maintaining the relatively short reaction duration positively affects strand-break and oxidation further. A concentration of less than 20 mM results in even less strand-break and oxidation, and a concentration of no more than 15 mM results in even less strand-break and oxidation, and a concentration of around 10 mM results in the least degree of strand-break and oxidation. As demonstrated in Example 5, the modified sulfamidase according to aspects described herein shows less strand-break, especially in the c-terminal part of the sulfamidase, as represented e.g. by amino acids 436-484 of SEQ ID NO:1. This c-terminal part has found to be intact in the sulfamidase prepared as described herein. Moreover, oxidation of methionine in position 226 (Met226) is less frequent.

In one embodiment, said periodate is sodium meta-periodate and is used at a (final) concentration of no more than 20 mM, such as no more than 15 mM, such as around 10 mM, and said reaction of step a) is performed for a time period of no more than 4 h, such as no more than 3 h, such as no more than 2 h, such as no more than 1 h, such as around 0.5 h at a temperature of between 0 and 22° C., such as around 8° C., such as around 0° C.

In one embodiment, said periodate is used at a concentration of no more than 20 mM, such as no more than 15 mM, such as around 10 mM, and said reaction of step a) is performed for a time period of no more than 4 h, such as no more than 3 h, such as no more than 2 h, such as no more than 1 h, such as around 0.5 h, at a temperature of between 0 and 22° C., such as a temperature of 0-8° C., such as a temperature of 0-4° C., such as around 8° C., such as around 0° C.

In one embodiment, said periodate is sodium meta-periodate and said reaction of step a) is performed for a time period of no more than 4 h, such as no more than 3 h, such as no more than 2 h, such as no more than 1 h, such as around 0.5 h at a temperature of between 0 and 22° C., such as a temperature of 0-8° C., such as a temperature of 0-4° C., such as around 8° C., such as around 0° C.

In one embodiment, said periodate is sodium meta-periodate which is used at a concentration of no more than 20 mM, such as no more than 15 mM, such as around 10 mM, and said reaction of step a) is performed at a temperature of between 0 and 22° C., such as a temperature of 0-8° C., such as a temperature of 0-4° C., such as around 8° C., such as around 0° C.

In one embodiment, said periodate is sodium meta-periodate which is used at a concentration around 10 mM, and said reaction of step a) is performed at a temperature of around 8° C. and for a time period of no more than 2 h.

In one embodiment, said periodate is sodium meta-periodate which is used at a concentration of around 10 mM, and said reaction of step a) is performed at a temperature of 0-8° C. and for a time period of no more than 3 h.

In the following paragraphs, specific embodiments of step b) are disclosed. It should be understood that unless defined otherwise, specific embodiments can be combined, in particular specific embodiments of step a) and step b).

In one embodiment, said alkali metal borohydride is sodium borohydride.

In some instances, the conditions used for step b) have been found to partly depend on the conditions used for step a). While the amount of borohydride used in step b) is preferably kept as low as possible, the molar ratio of borohydride to periodate is in such instances 0.5-4 to 1. Thus, borohydride may in step b) be used in a molar excess of 4 times the amount of periodate used in step a). In one embodiment, said borohydride is used at a (final) molar concentration of no more than 4 times the (final) concentration of said periodate. For example, borohydride may be used at a concentration of no more than 3 times the concentration of said periodate, such as no more than 2.5 times the concentration of said periodate, such as no more than 2 times the concentration of said periodate, such as no more than 1.5 times the concentration of said periodate, such as at a concentration roughly corresponding to the concentration of said periodate. However, in particular embodiments borohydride is used at a concentration corresponding to half of the periodate concentration, or 0.5 times the periodate concentration. Thus, when periodate is used at a concentration of around 20 mM, borohydride might be used at a concentration of no more than 80 mM, or even at a concentration between 10 and 80 mM, such as at a concentration of between 10 and 50 mM. If periodate is used at a concentration of between 10 and 20 mM, borohydride might be used at a concentration of between 25 and 80 mM, such as for example 50 mM. Similarly, if periodate is used at a concentration of around 10 mM, borohydride might be used at a concentration of no more than 40 mM, such as for example no more than 25 mM. Moreover, in such an embodiment, borohydride may preferably be used at a concentration of between 12 mM and 50 mM. The inventors have found that the concentration of borohydride influence the degree of preservation of a catalytic amino acid residue at the active site of sulfamidase, and thus that a relatively lower concentration of borohydride may provide a modified sulfamidase having retained catalytic activity.

In one embodiment, said reaction of step b) is performed for a time period of no more than 1.5 h, such as no more than 1 h, such as no more than 0.75 h, such as around 0.5 h. The reaction duration is preferably around 1 h, or less than 1 h. In some instances, the reaction of step b) has a duration of approximately 0.25 h. In further embodiments, the reaction of step b) may be performed for a time period of from 0.25 h to 2 h. As accounted for above, the duration of the reduction step has been found to affect the catalytic activity of the sulfamidase. A relatively short reaction duration may thus provide a modified sulfamidase comprising FGly50 rather than Ser50. A shorter reaction duration moreover has been found to favorably influence the overall structural integrity of the enzyme. In particular, protein aggregation resulting in high molecular weight forms of sulfamidase as well as strand-break occurrence seem at least partly related to reaction time. Thus, a relatively short reaction duration for step b) may reduce the occurrence of aggregates as well as strand-breaks. As accounted for elsewhere in this text, reduced presence of aggregated forms may render a protein more suitable for use in therapy.

In one embodiment, said reaction of step b) is performed at a temperature of between 0 and 8° C. Reaction temperature for step b) has been found to at least partly affect catalytic activity of the reaction product. In particular, conversion of a catalytic residue in the active site of sulfamidase is related to reaction temperature. Thus, it may be advantageous to perform step b) at a temperature of below 8° C. The temperature is preferably around 0° C.

In one embodiment, said alkali metal borohydride is sodium borohydride which is used at a concentration of 0.5-4 times the concentration of said periodate, such as at a concentration of no more than 2.5 times the concentration of said periodate.

In one embodiment, said alkali metal borohydride is sodium borohydride which is used at a concentration of 0.5-4 times the concentration of said periodate, such as at a concentration of no more than 2.5 times the concentration of said periodate, and said reaction of step b) is performed for a time period of no more than 1 h, such as around 0.5 h.

In one embodiment, said alkali metal borohydride is sodium borohydride which is used at a concentration of 0.5-4 times the concentration of said periodate, such as at a concentration of no more than 2.5 times the concentration of said periodate, and said reaction of step b) is performed for a time period of no more than 1 h, such as around 0.5 h, at a temperature of between 0 and 8° C.

In one embodiment, said alkali metal borohydride is used at a concentration of 0.5-4 times the concentration of said periodate, such as at a concentration of no more than 2.5 times the concentration of said periodate, and said reaction of step b) is performed for a time period of no more than 1 h, such as around 0.5 h, at a temperature of between 0 and 8° C.

In one embodiment, said alkali metal borohydride is sodium borohydride, and said reaction of step b) is performed for a time period of no more than 1 h, such as around 0.5 h, at a temperature of between 0 and 8° C.

In one embodiment, said alkali metal borohydride is sodium borohydride which is used at a concentration of 0.5-4 times the concentration of said periodate, such as at a concentration of no more than 2.5 times the concentration of said periodate, and said reaction of step b) is performed at a temperature of between 0 and 8° C.

In one embodiment, said alkali metal borohydride is sodium borohydride which is used at a concentration of 0.5-4 times the concentration of said periodate, such as at a concentration of 2.5 times the concentration of said periodate, and said reaction of step b) is performed at a temperature of around 0° C. for a time period of around 0.5 h.

In one embodiment, said periodate is sodium meta-periodate and said alkali metal borohydride is sodium borohydride.

In one embodiment, each of step a) and step b) is individually performed for a time period of no more than 2 h, such as no more than 1 h, such as around 1 h or around 0.5 h. Optionally, said borohydride is used at a concentration of 0.5-4 times the concentration of said periodate, preferably 0.5-2.5 times the concentration of said periodate. In certain embodiments, said borohydride is used at a concentration of 0.5 times the concentration of the periodate, or at a concentration of 2.5 times the concentration of said periodate.

In one embodiment, step a) is performed for a time period of no more than 3 h and step b) is performed for no more than 1 h. Optionally, said borohydride is used at a concentration of no more than 4 times the concentration of said periodate, preferably no more than 2.5 times the concentration of said periodate.

The person skilled in the art is aware of ways to control the reaction duration of a chemical reaction, such as the reaction duration of each of step a) and b). Thus, in one embodiment, said method aspect further comprises a2) quenching of the reaction resulting from step a). Said quenching for example has a duration of less than 30 minutes, such as less than 15 minutes. In some instances, said quenching is performed immediately after step a). Quenching may for example be performed by addition of ethylene glycol. Ethylene glycol may be added to a final concentration of 192 mM. Preferably, step b) follows immediately after the quenching. This may minimize the period of exposure for sulfamidase to reactive aldehyde groups. Reactive aldehydes can promote inactivation and aggregation of the protein.

In one embodiment, said method further comprises b2) quenching of the reaction resulting from step b). This quenching may for example be conducted by addition of a molecule that contains a ketone or aldehyde group, such as cyclohexanone or acetone, said molecule preferably being soluble in water. Alternatively, said quenching may be conducted by lowering the pH below 6 of the reaction mixture by addition of acetic acid or another acid. In some instances, said quenching is performed by addition of acetone to a final concentration of around 0.1 M. An optional quenching step allows for a precise control of reaction duration for step b). Controlling reaction duration in this way may further provide reproducibility of the process in terms of FGly50 content.

The method as disclosed herein thus provides a modified sulfamidase having a number of advantages over sulfamidase modified according to prior art. The inventors thus have found conditions for chemical modification of sulfamidase with minimal negative impact on structural integrity of the sulfamidase polypeptide chain, simultaneously resulting in substantial absence of natural glycan structures suggesting a nearly complete modification of glycans at all four natural glycosylated sites while retaining catalytic activity. Surprisingly, in particular example the conditions used for step a) were found to facilitate the conditions for performing step b). Exemplary embodiments of the method are depicted in FIGS. 1B, 1C and 1D.

In one aspect, there is provided a modified sulfamidase obtainable by the method according to the above defined method aspect.

In one aspect, there is provided a modified sulfamidase obtainable by the method aspect as described above for use in therapy.

In one aspect, there is provided a modified sulfamidase obtainable by the method aspect as described above for use in treatment of lysosomal storage disease, in particular mucopolysaccharidosis IIIA (MPS IIIA).

In one aspect, use of a modified sulfamidase in the manufacture of a medicament is provided, for crossing the blood brain barrier to treat a lysosomal storage disease, such as mucopolysaccharidosis IIIA (MPS IIIA), in a mammalian brain, said modification comprises having glycan moieties chemically modified by sequential treatment of the enzyme with an alkali metal periodate and an alkali metal borohydride, thereby reducing the activity of the sulfamidase with respect to glycan recognition receptors, such as mannose and mannose-6-phosphate cellular delivery systems, while retaining catalytic activity of said sulfamidase.

In one aspect there is provided a method of treating a mammal afflicted with a lysosomal storage disease, such as mucopolysaccharidosis IIIA (MPS IIIA), comprising administering to the mammal a therapeutically effective amount of a modified sulfamidase, said modified sulfamidase being selected from:

a) a modified sulfamidase as described in aspects and embodiments herein;

b) a sulfamidase composition as described in aspects and embodiments herein, and c) a modified sulfamidase wherein the modification comprises sequential treatment of said modified sulfamidase with an alkali metal periodate and an alkali metal borohydride, whereby the sulfamidase has its glycan moieties chemically modified so as to reduce its activity with respect to glycan recognition receptors, such as mannose and mannose 6-phosphate cellular delivery systems, while retaining catalytic enzymatic activity.

In one embodiment thereof, said treatment results in clearance of about at least 48% lysosomal storage from the brain of a mammal after administration of 10 doses of modified sulfamidase over a time period of 70 days. In addition, said treatment results in clearance of about at least 30% lysosomal storage from the brain of a mammal after administration of 13 doses of modified sulfamidase over a time period of 25 days.

The invention will be further illustrated by the following non-limiting examples.

BRIEF DESCRIPTION OF THE DRAWINGS

FIGS. 1A-1D are a picture outlining the differences between the methods for chemical modification developed by the inventors, disclosed in Example 4, and the known method, disclosed in WO 2008/109677.

FIG. 11 is a table listing amino acid sequences of human sulfamidase, wherein SEQ ID NO:1 corresponds to the amino acid sequence of human sulfamidase, SEQ ID NO:2 corresponds to GS-sulfamidase, and SEQ ID NO:3 corresponds to sulfamidase-GS.

EXAMPLES

Figure 2B:
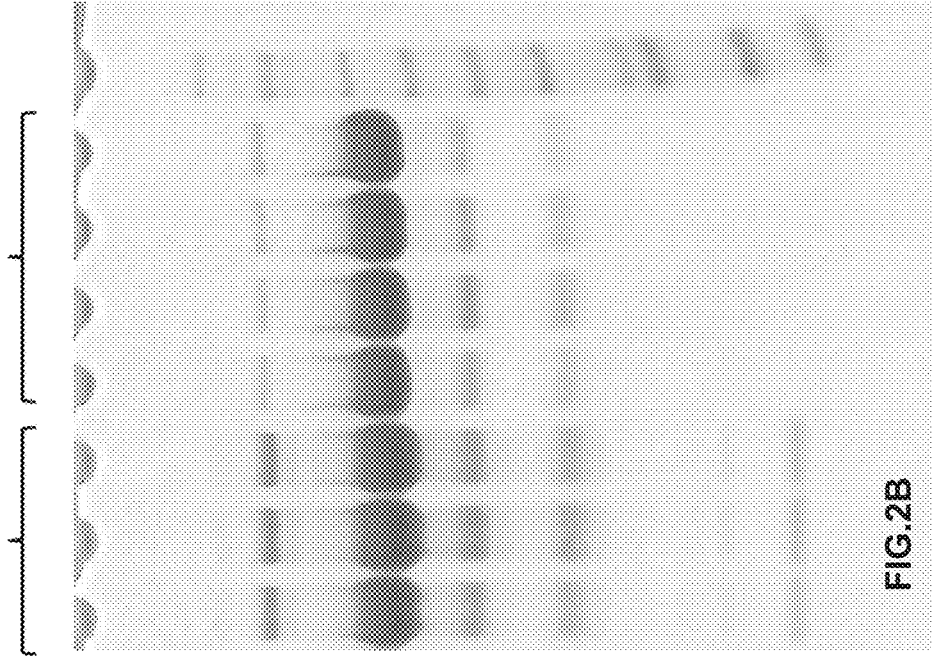
FIG. 2B shows a SDS-PAGE gel of both sulfamidase modified according to the known method as well as sulfamidase modified according to new method 1 as disclosed herein.

The examples which follow disclose the development of a modified sulfamidase polypeptide according to the present disclosure.

Example 1

Cultivation, Purification and Characterization of Sulfamidase

Material and Methods
Construction of Expression Vectors for Sulfamidase:

Synthetic genes encoding human sulfamidase were synthesized by Geneart (Life Technologies), both in codon optimized versions for *H. sapiens* or *C. griseus* (CHO cells) and the original human sequence. The synthetic genes were cloned in different mammalian expression vectors, such as pcDNA3.1(+) (Invitrogen) or pQMCF1 (Icosagen).

Production of Sulfamidase:

Two transient expression systems were evaluated for sulfamidase production, transient expression in HEK293 cells using pcDNA3.1(+) vectors and the Quattromed Cell Factory (QMCF) episomal expression system (Icosagen AS) using the pQMCF1 vector. In both systems cells were grown in standard medium and secreted protein was harvested typically 6-8 days after transfection. In addition, a stable cell line established using a commercially available CHO expression system was evaluated for production of sulfamidase.

Sulfamidase was captured from medium by anion exchange chromatography (AIEX) on a Q sepharose column (GE Healthcare) equilibrated with 20 mM Tris, 1 mM EDTA, pH 8.0 and eluted by a NaCl gradient. Captured sulfamidase was further purified by 4-Mercapto-Ethyl-Pyridine (MEP) chromatography; sulfamidase containing fractions were loaded on a MEP HyperCel chromatography column and subsequently eluted by isocratic elution in 50 mM NaAc, 0.1 M NaCl, 1 mM EDTA, 1 mM DTT, pH 4.6. Final polishing was achieved by cation exchange chromatography (CIEX) on a SP Sepharose FF (GE Healthcare) column equilibrated in 25 mM NaAc, 2 mM DTT, pH 4.5. A NaCl gradient was used for elution. Purity and identity of sulfamidase batches from the different expression systems were analyzed by SDS-PAGE and MALDI-TOF-MS, data not shown.

Glycosylation Analysis:

The glycosylation pattern was determined for the different sulfamidase batches produced. Prior to glycopeptide analysis, sulfamidase (ca 10 µg) was reduced, alkylated and digested with trypsin. Reduction of the protein was done by incubation in 5 µl DTT 10 mM in 50 mM $NH_4HCO_3$ at 70° C. for 1 h. Subsequent alkylation with 5 µl iodoacetamide 55 mM in 50 mM $NH_4HCO_3$ was performed at room temperature (RT) and in darkness for 45 min. Lastly, the tryptic digestion was performed by addition of 30 µl of 50 mM $NH_4HCO_3$, 5 mM $CaCl_2$, pH 8, and 0.2 µg/µl trypsin in 50 mM acetic acid (protease: protein ratio 1:20 (w/w)). Digestion was allowed to take place over night at 37° C.

Five peptide fragments of the trypsin digested sulfamidase contained potential N-glycosylation sites. These peptide fragments containing potential glycosylation sites N(x), where x refers the position of the asparagine in the sulfamidase amino acid sequence as defined in SEQ ID NO:1, were:
N(21) containing fragment (residue 4-35 of SEQ ID NO:1, 3269.63 Da)
N(122) containing fragment (residue 105-130 of SEQ ID NO:1, 2910.38 Da)
N(131) containing fragment (residue 131-134 of SEQ ID NO:1, 502.29 Da)
N(244) containing fragment (residue 239-262 of SEQ ID NO:1, 2504.25 Da)
N(393) containing fragment (residue 374-394 of SEQ ID NO:1), 2542.22 Da The asparagine of each potential glycosylation site is indicated in bold and the molecular mass of each peptide fragment is given.

Possible glycosylation variants of the five tryptic peptide fragments were investigated by glycopeptide analysis. This was performed by liquid chromatography followed by mass spectrometry (LC-MS) on an Agilent 1200 HPLC system coupled to an Agilent 6510 Quadrupole time-of-flight mass spectrometer (Q-TOF-MS). Both systems were controlled by MassHunter Workstation. LC separation was performed by the use of a Waters XSELECT CSH 130 C18 column (150×2.1 mm), the column temperature was set to 40° C. Mobile phase A consisted of 5% acetonitrile, 0.1% propionic acid, and 0.02% TFA, and mobile phase B consisted of 95% acetonitrile, 0.1% propionic acid, and 0.02% TFA. A gradient of from 0% to 10% B for 10 minutes, then from 10% to 70% B for another 25 min was used at a flow rate of 0.2 mL/min. The injection volume was 10 μl. The Q-TOF was operated in positive-electrospray ion mode. During the course of data acquisition, the fragmentor voltage, skimmer voltage, and octopole RF were set to 90, 65, and 650 V, respectively. Mass range was between 300 and 2800 m/z.

Results

Transient expression in HEK293 cells resulted in low levels of secreted sulfamidase (less than 0.3 mg/L medium, SEQ ID NO:3). The QMCF stabile episomal expression system (Icosagen AS), resulted in sulfamidase (SEQ ID NO:2) production in titers of above 10 mg/L in CHO cells. The stable cell line established from a CHO expression system resulted in sulfamidase (SEQ ID NO:1) titers in excess of 40 mg/L.

Sulfamidase was purified to apparent homogeneity with a molecular mass in the 61-63 kDa range. Based on the theoretical peptide chain mass of 55 kDa this indicates the presence of glycans with a total molecular mass of 6-8 kDa. Purity and identity of sulfamidase batches were analyzed by SDS-PAGE and MALDI-TOF-MS (results not shown).

Glycosylation analysis for the tryptic digested peptides was performed by LC-MS. Manual search for 30 different kinds of glycosylation on each glycopeptide was performed. Relative quantitation was performed by measuring the peak areas from reconstructed ion chromatograms (without correction for ionization efficiency). Four of the five putative N-glycosylation sites (N(21), N(131), N(244) and N(393)) were glycosylated consistently through all sulfamidase batches. N(21) and N(393) were predominantly occupied by complex glycans, with a low degree of full sialylation. N(131) were completely occupied by oligomannose type of glycans. The degree of glycan phosphorylation was roughly 50% for all batches. The N(131) site was resistant to dephosphorylation by alkaline phosphatase. The fourth site, N(244), differed in composition between CHO cell (SEQ ID NO:2) and HEK293 cell (SEQ ID NO:3) produced sulfamidase by being oligomannose in CHO batches and a oligomannose/complex mixture in HEK293 batches. The tryptic peptide containing N(122) was found without any glycans attached.

Example 2

Chemical Modification of Sulfamidase According to Previously Known Method

Material and Methods
Chemical Modification According to the Known Method (as Disclosed in WO 2008/109677):

In order to modify glycan moieties of sulfamidase, sulfamidase (SEQ ID NO:2), produced as described in Example 1 in Quattromed Cell Factory (QMCF) episomal expression system (Icosagen AS), was initially incubated with 20 mM sodium meta-periodate at 0° C. for 6.5 h in 20 mM sodium phosphate, 100 mM NaCl (pH 6.0). Glycan oxidation was quenched by addition of ethylene glycol to a final concentration of 192 mM. Quenching was allowed to proceed for 15 min at 0° C. before performing dialysis against 20 mM sodium phosphate, 100 mM NaCl (pH 6.0) over night at 4° C. Following dialysis, reduction was performed by addition of sodium borohydride the reaction mixture to a final concentration of 100 mM. The reduction reaction was allowed to proceed over night. Finally, the enzyme preparation was dialyzed against 20 mM sodium phosphate, 100 mM NaCl (pH 7.5). All incubations were performed in the dark.

Results

Modified sulfamidase was produced in triplicates in accordance with the sequence of steps depicted in FIG. 1A.

Example 3

Analyses of Sulfamidase Modified According to Known Method

Material and Methods
The sulfamidase modified according to Example 2, corresponding to the known method, was subjected to the following analyses.
SDS-PAGE Analysis:
5 μg of modified sulfamidase was loaded into each well on a NuPAGE 4-12% Bis-Tris gel. Seeblue 2 plus marker was used and the gel was colored with Instant Blue (C.B.S Scientific).
Analysis by Size Exclusion Chromatography (SEC):
The modified enzyme was analyzed by analytical size exclusion chromatography, performed on a ÄKTAmicro system (GE Healthcare). A Superdex 200 PC 3.2/30 column with a flow rate of 40 μL/min of formulation buffer was used. The sample volume was 10 μL and contained 10 μg enzyme.
Dynamic Light Scattering (DLS) Analysis:
The modified sulfamidase was degassed by centrifugation at 12000 rpm for 3 min at room temperature (RT). DLS experiments were performed on a DynaPro Titan instrument (Wyatt Technology Corp) using 25% laser power with 3 replicates of 75 μL each.
In-Gel Digestion and MALDI-TOF MS Analysis:
The SDS-PAGE analysis revealed some extra bands, which were excised, destained and processed by in-gel digestion with trypsin. The procedure was the following:
  i. Coomassie destaining: the excised gel bands were placed in eppendorf tubes. The tubes were agitated twice in 100 mM NH$_3$HCO$_3$ in 50% acetonitrile at 30° C. for 1 h. The supernatants were discarded.

ii. Reduction and alkylation: the gel pieces were dehydrated in acetonitrile, dried in a Speed Vac, and subsequently covered with 10 mM DTT in 100 mM NH$_3$HCO$_3$. Reduction was allowed to proceed for 1 h at 57° C. The supernatant was discarded and replaced by 55 mM iodoacetamide in 100 mM NH$_3$HCO$_3$. Alkylation was performed for 45 min at RT, in darkness and under slight agitation. The supernatant was once again discarded. The gel was washed with 100 mM NH$_3$HCO$_3$ in 50% acetonitrile for 20-30 min at 30° C., whereafter the supernatant was discarded. The gel pieces were dried completely in a Speed Vac.

iii. In-gel digestion with trypsin: 2-5 µL 50 mM NH$_3$HCO$_3$ was added to the dried gel pieces, whereafter 5 µL trypsin solution (0.1 µg/µL in 1% acetic acid) was added. More 50 mM NH$_3$HCO$_3$ was added to cause swelling of the gel. Digestion was performed over night at 37° C. (with agitation). The supernatant was transferred to a new tube and extracted with 60% acetonitrile, 0.1% TFA (3×20 min) at RT. The resulting supernatants were evaporated in a Speed Vac to near dryness. The concentrated solution was mixed 1:1 with alpha-cyano-4-hydroxycinnamic acid solution (10 mg/mL) and 0.6 µL was applied on a MALDI plate.

Molecular masses of the tryptic peptide fragments were determined using a Sciex 5800 matrix-assisted laser desorption/ionization-time-of-flight mass spectrometer (MALDI-TOF/TOF MS). The analyses were performed in positive ion reflectron mode with a laser energy of 3550 and 400 shots.

Preservation of Active Site:

Any effect of the chemical modification on the active site of sulfamidase was investigated by the use of LC-MS and LC-MS/MS analyses. The samples were prepared according to the LC-MS method described under section Glycosylation analysis in Example 1. The resulting tryptic peptides containing cysteine 50 variants (cysteine50 (alkylated), oxidized cysteine 50, FGly50 and Ser50) were all semiquantified using peak area calculations from reconstructed ion chromatograms. The identity of the peptides were performed by MSMS sequencing. The MSMS parameters were as follows: the collision energies were set to 10, 15, and 20V, scan range 100-1800 m/z, and scan speed 1 scan/sec.

Results

Figure 2A:
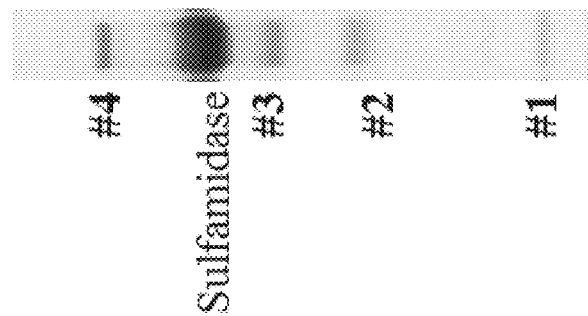
FIG. 2A shows a SDS-PAGE gel of sulfamidase modified according to the known method. Four protein bands, denoted 1-4, generated by the glycan modification procedure were identified.

SDS-PAGE Analysis:

As apparent by SDS-PAGE analysis, several peptides of sizes distinct from that of full length sulfamidase were formed as a result of the chemical modification (FIG. 2A).

Figure 3A:
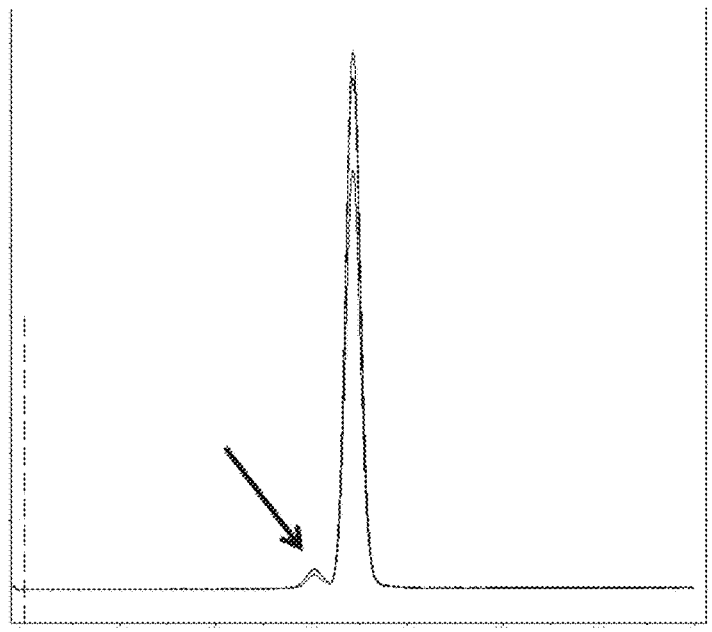
FIG. 3A shows a SEC chromatogram of sulfamidase modified according to the known method.

Analysis by SEC and DLS:

The chemical modification procedure was found to promote aggregation of sulfamidase, as demonstrated as a pre-peak in the chromatogram of FIG. 3A. The peak height of the pre-peak in the chromatogram was found to be approximately 3% of the height of the main peak.

Figures 4A, 4B:
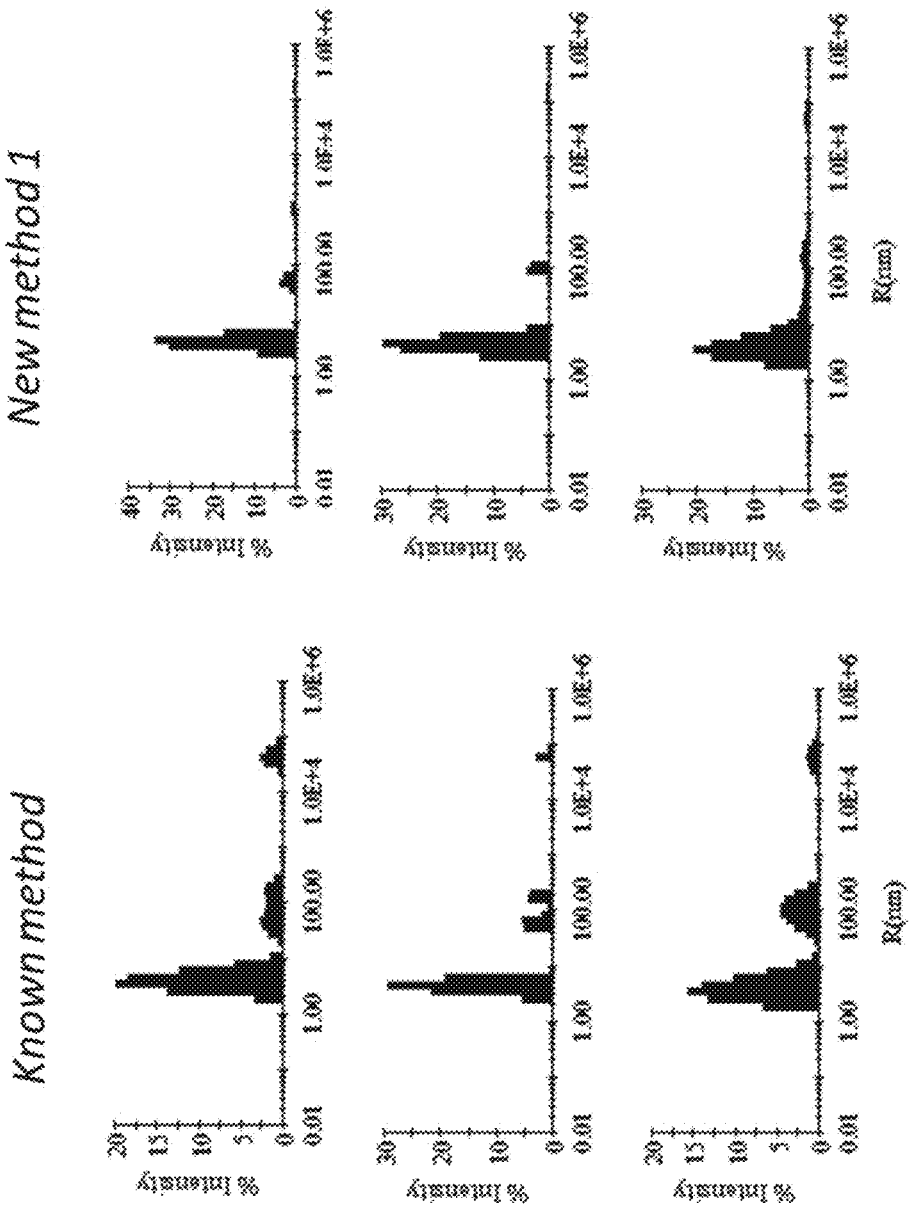
FIG. 4A shows scattering intensity measured by dynamic light scattering of sulfamidase modified according to the known method.
FIG. 4B shows scattering intensity measured by dynamic light scattering of sulfamidase modified according to new method 1 as described herein.

The DLS analysis moreover revealed that the same material contained 15-20% of protein of the total protein content in high molecular weight forms (i.e. above $10^{10}$ kDa) (FIG. 4A).

Analysis of SDS-PAGE Bands:

By MALDI-TOF MS analysis, the four gel bands #1-4 observed on SDS-PAGE (FIG. 2A) could be identified as fragments of sulfamidase generated by strand breaks during the chemical modification.

The gel bands #1 and #2 of FIG. 2A were determined as two C-terminal truncations with molecular masses of 6 kDa and 30 kDa, gel band #3 as one 41 kDa N-terminal truncation, and gel band #4 as one dimeric form of sulfamidase (111 kDa band), formed as a result of the chemical modification (MALDI spectra not shown).

Thus, it was found that chemical modification of sulfamidase in accordance with the known method not only modifies glycans but also generates strand breaks at specific positions in the sulfamidase polypeptide chain.

It was also found that the chemical modification according to the known method introduces oxidation on several methionine residues on sulfamidase, in particular on methionine 184 and methionine 443, which were almost completely oxidized. Methionine 226 (found in tryptic peptide T23, which corresponds to amino acid residues 226-238) was oxidized to a much lower degree, but this oxidation appeared to give rise to a more unstable protein than sulfamidase as such, generating the 41 kDa N-terminal truncation (gel band#3 of FIG. 2A). Thus, oxidation of methionine 226 and strand breaks seemed to be correlated, as observed in the MS analysis. In addition, the dimer band (#4 of FIG. 2A) also predominantly contained oxidized methionine 226 (FIG. 2A).

Consequently, the known procedure for modification of glycans catalyses oxidation of amino acid residues crucial for structural integrity of the enzyme.

Preservation of Active Site:

Moreover, by the use of LC-MSMS the reduction step (FIG. 1A) was found to reduce the FGly residue at the active site position 50 of SEQ ID NO:1 to Ser. Ser in this position is not compatible with efficient catalysis (Recksiek et al, J Biol Chem 273(11):6096-103 (1998)). The relative amount Ser produced from FGly was estimated based on peak area measurements of the doubly charged ions in the mass spectrum, corresponding to the two tryptic peptide fragments containing FGly50 and Ser50. The peak areas were based on MS response without correction for ionization efficiency. Table 1 below shows that the conversion of FGly to Ser is approximately 56% after modification according to the known method (see also Example 5, Table 2).

TABLE 1

Conversion of FGly to Ser at active site

| Chemical modification of sulfamidase | Ser formation (%) | FGly/Ser ratio |
| --- | --- | --- |
| None | 0 | |
| Known method | 56.0 ± 0.3 (n = 3) | 0.8 |

Thus, the known chemical modification procedure, in addition to the modifications mentioned above, causes reduction of amino acid residues crucial for catalytic activity of the enzyme.

Example 4

New Methods for Chemical Modification of Sulfamidase

Material and Methods

New Method 1:

Sulfamidase produced in Quattromed Cell Factory (QMCF) episomal expression system (Icosagen AS) according to Example 1, was oxidized by incubation with 20 mM sodium meta-periodate at 0° C. in the dark for 120 min in phosphate buffers having a pH of 6.0. Glycan oxidation was quenched by addition of ethylene glycol to a final concentration of 192 mM. Quenching was allowed to proceed for 15 min at 6° C. before sodium borohydride was added to the reaction mixture to a final concentration of 50 mM. After incubation at 0° C. for 120 min in the dark, the resulting sulfamidase preparation was ultrafiltrated against 20 mM sodium phosphate, 100 mM NaCl, pH 6.0. The new method 1 for chemical modification is depicted in FIG. 1B.

New Method 2:

Performed as New method 1 with the exception that the concentration of sodium borohydride in the reduction step was 10 mM. The new method 2 for chemical modification is depicted in FIG. 1C.

New Method 3:

Sulfamidase produced in a stable cell line according to Example 1 was oxidized by incubation with 10 mM sodium meta-periodate at 0° C. in the dark for 180 min in acetate buffer having an initial pH of between 4.5 to 5.7. Glycan oxidation was quenched by addition of ethylene glycol to a final concentration of 192 mM. Quenching was allowed to proceed for 15 min at 6° C. before sodium borohydride was added to the reaction mixture to a final concentration of 25 mM. After incubation at 0° C. for 60 min in the dark, the resulting sulfamidase preparation was ultrafiltrated against 10 mM sodium phosphate, 100 mM NaCl, pH 7.4. The new method 3 for chemical modification is depicted in FIG. 1D.

New Method 4:

Sulfamidase produced in a stable cell line according to Example 1 was oxidized by incubation with 10 mM sodium meta-periodate at 8° C. in the dark for 60 min in acetate buffer having an initial pH of 4.5. Glycan oxidation was quenched by addition of ethylene glycol to a final concentration of 192 mM. Quenching was allowed to proceed for 15 min at 6° C. before sodium borohydride was added to the reaction mixture to a final concentration of 25 mM. After incubation at 0° C. for 60 min in the dark, the resulting sulfamidase preparation was ultrafiltrated against 10 mM sodium phosphate, 100 mM NaCl, pH 7.4.

Investigation of a Second Quenching Step:

The effect of quenching the second step was investigated by the addition of 0.1 M Acetone after the sodium borohydride incubation step in new method 1. Material was produced in parallel according to new method 1 up to and including the sodium borohydride addition and incubation, after that reaction in one sample was quenched by the addition of acetone. Both samples were then treated according to the ultrafiltration step in new method 1.

New Method 5:

Sulfamidase produced in a stable cell line according to Example 1 was oxidized by incubation with 10 mM sodium meta-periodate at 8° C. in the dark for 60 min in acetate buffer having an initial pH of 4.5. Glycan oxidation was quenched by addition of ethylene glycol to a final concentration of 192 mM. Quenching was allowed to proceed for 15 min at 6° C. before sodium borohydride was added to the reaction mixture to a final concentration of 25 mM. After incubation at 0° C. for 45 min in the dark and quenching the reaction with 0.1 M acetone, the resulting sulfamidase preparation was ultrafiltrated against 10 mM sodium phosphate, 100 mM NaCl, pH 7.4.

Results

As already accounted for elsewhere herein, sodium meta-periodate is an oxidant that converts cis-glycol groups of carbohydrates to aldehyde groups, whereas borohydride is a reducing agent that reduces the aldehydes to more inert alcohols. The carbohydrate structure is thus irreversibly destroyed.

In order to provide an improved method for chemical modification of glycans, in particular a procedure that provides a modified sulfamidase with improved properties, different reaction conditions were evaluated. It could be concluded that both oxidation by sodium meta-periodate and reduction by sodium borohydride introduced polypeptide modifications and aggregation; properties that negatively impact on catalytic activity and immunogenic propensity.

Conditions were discovered for an improved chemical modification procedure. Surprisingly, these conditions facilitated that the reduction step could be performed immediately after the ethylene glycol quenching step, omitting buffer change and long exposure of sulfamidase to reactive aldehyde intermediates. The new chemical modification procedures are depicted in FIG. 1B, FIG. 1C and FIG. 1D.

Example 5

Analyses of Sulfamidase Modified According to New Methods

Material and Methods

The sulfamidase modified according to the new methods of Example 4 were subjected to the following analyses.

SDS-PAGE Analysis:

5 µg of sulfamidase modified in accordance with the known method (Example 2) as well as with the new method 1 and 2 (Example 4) were loaded into separate individual wells in accordance with the description in Example 3. Similarly, 5 µg of sulfamidase modified in accordance with the new method 1 (Example 4) as well as with the new method 3, 4 and 5 were loaded into separate individual wells in accordance with the description in Example 3.

Analysis by Size Exclusion Chromatography (SEC):

Sulfamidase modified according to new method 1-4 was analyzed by analytical size exclusion chromatography in accordance with Example 3.

Dynamic Light Scattering (DLS) Analysis:

Sulfamidase modified according to new method 1 was analyzed by DLS in accordance with Example 3.

Preservation of Active Site:

Any effect of the chemical modification on the active site of sulfamidase, produced according to new method 1-5, as well as the second investigated quenching step was investigated in accordance with the description in Example 3.

Results

SDS-PAGE Analysis:

Several peptides of sizes distinct from that of full length sulfamidase were formed as a result of the new chemical modification method 1 (FIG. 2B). However, compared to the sulfamidase modified according to the known method, the new method 1 gave rise to less fragmentation. Fragment #1 (FIG. 2A), identified as the C-terminal amino acids 434-482, was not detectable in sulfamidase samples generated by the new methods 1, 3, and 4 and the amounts of the other fragments were greatly reduced. This trend was even more pronounced in the material produced by the new method 2. However with new method 2, there was more high molecular weight forms present on the gel, indicating that the amount of reducing agent was not sufficient to reduce all the reactive aldehydes generated in the oxidation step (data not shown). New methods 3, 4 and 5 produced a modified sulfamidase material that was similar to the one produced by new method 1 (data not shown).

Strand-breaks in the sulfamidase polypeptide prepared by the new methods is thus limited compared to strand-break occurrence in the sulfamidase prepared according to Example 2.

Figure 3B:
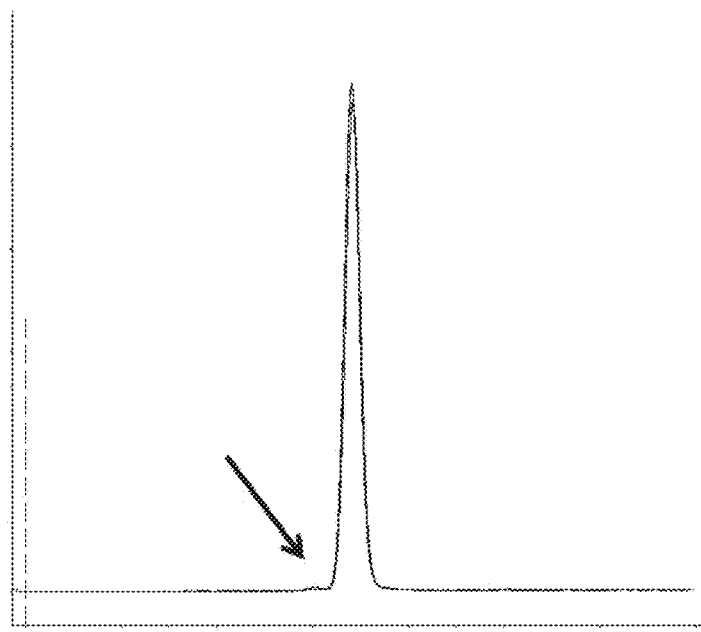
FIG. 3B shows a SEC chromatogram of sulfamidase modified according to new method 1 as disclosed herein. Marked by an arrow is the amount of multimeric forms of modified sulfamidase.

Analysis by Size Exclusion Chromatography (SEC):

It was found that the sulfamidase modified according to the new method 1 contained less aggregates compared to the sulfamidase modified by the known method. This is demonstrated in the chromatograms of FIGS. 3A-3B, where the high molecular weight form is present in the chromatogram as a pre-peak. The peak height of the pre-peak in FIG. 3B is 0.5%, relative the main peak height, thus representing a decrease compared to peak height (3%) in FIG. 3A. This is also the case for sulfamidase modified by new method 3, 4 and 5 (data not shown).

Dynamic Light Scattering (DLS) Analysis:

The DLS analysis (FIG. 4B) confirmed the results from SEC analysis: the sulfamidase produced according to the new method contained 5% protein in high molecular weight forms (above $10^{10}$ kDa). It could thus be concluded that formation of aggregated forms of sulfamidase is limited by the new methods compared to the known method (see Example 3).

Preservation of Active Site:

The reduction of FGly to Ser in position 50 at the active site of sulfamidase was determined by LC-MS/MS and the tryptic peptides containing FGly and Ser were positively identified. The relative amount of the peptide fragments was analyzed with LC-MS by measuring the peak areas from reconstructed ion chromatograms of the doubly charged ions (without correction for ionization efficiency). The samples generated from the methods used in Example 4 for the chemical modification were prepared and analyzed. (Table 2).

TABLE 2

Conversion of FGly to Ser at active site

| Chemical modification of sulfamidase | Ser formation (%) | FGly/Ser ratio |
| --- | --- | --- |
| None | 0 | |
| New method 1 | 45.4 ± 0.9 (n = 3) | 1.2 |
| New method 2 | 11.5 ± 1.3 (n = 3) | 7.7 |
| New method 3 | 44.1 ± 2.0 (n = 2) | 1.2 |
| New method 4 | 36.1 (n = 1) | 1.6 |
| New method 5 | 41.7 ± 1.1 (n = 2) | 1.4 |

Loss of active site FGly is limited considerably by the new methods. The new methods of modifying glycans on sulfamidase significantly decreased the amount of Ser formation, from 56% using the known method (see Table 1, Example 3), to 45%, 44%, 36% and 42% (new method 1, 3, 4 and 5, respectively, Table 2). The Ser formation of the new method 2 was about 11%, thus indicating that the conversion of FGly to Ser was highly dependent on sodium borohydride concentration.

The second quenching step of the reaction provided modified sulfamidase comparable to the sulfamidase produced without quenching the reaction (modified sulfamidase produced according to new method 1 has 45% Ser formation compared to 43% Ser formation after quenching the second reaction with acetone). This was further confirmed by new method 5, which also encompasses a quenching step.

Example 6

Receptor Mediated Endocytosis In Vitro

Material and Methods

Sulfamidase was prepared as described in Example 1, 2 and 4, produced in Quattromed Cell Factory (QMCF) episomal expression system (Icosagen AS) and modified according to the known method and new methods 1 and 2 Endocytosis was evaluated in MEF-1 fibroblasts expressing M6P receptors. The MEF-1 cells were incubated for 24 h in DMEM medium supplemented with 75 nM of sulfamidase. The cells were washed twice in DMEM and once in 0.9% NaCl prior to cell lysis using 1% Triton X100. Lysate sulfamidase activity and total protein content were determined and lysate specific activity was calculated. Activity was monitored by fluorescence intensity at 460 nm using 0.25 mM 4-methylumbelliferyl-alpha-D-N-sulphoglucosaminide as substrate in 14.5 mM diethylbarbituric acid, 14.5 mM sodium acetate, 0.34% (w/v) NaCl, and 0.1% BSA. Total protein concentration was determined using the BCA kit (Pierce) with BSA as standard. Data are presented as mean+SD (n=4).

Results

Figure 5:
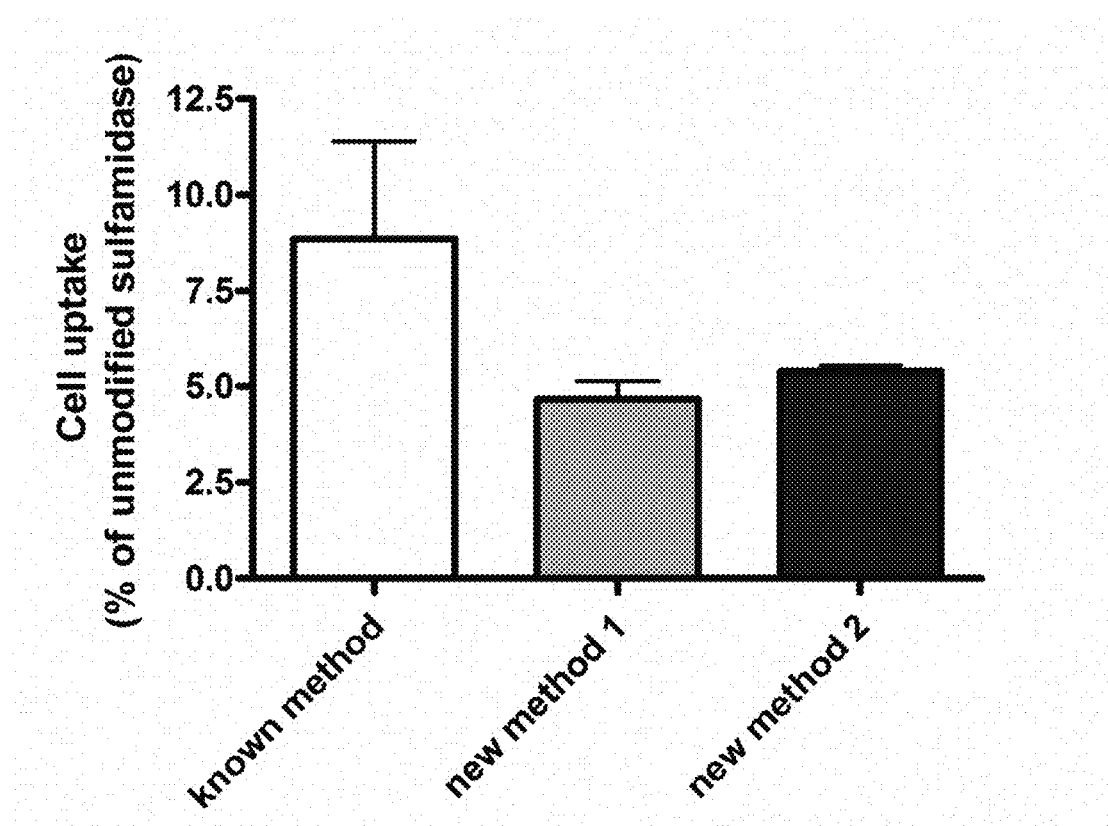
FIG. 5 is a diagram visualizing the receptor mediated endocytosis in MEF-1 cells of unmodified recombinant sulfamidase, sulfamidase modified according to the known method, and sulfamidase modified according to new method 1 and 2 as described herein.

Sulfamidase activity could be detected in cell homogenate for all preparations evaluated in the endocytosis assay. Modified sulfamidase prepared by the known method as well as the new methods 1 and 2 showed specific activities in cell homogenate below 10% of that obtained with unmodified recombinant sulfamidase (FIG. 5). The activity retained in cells first loaded with and then grown in the absence of sulfamidase for 2 days were comparable for all preparations showing that chemical modification do not negatively impact on lysosomal stability.

It can therefore be concluded that chemical modification render sulfamidase less prone to cellular uptake which is a consequence of removal of epitopes for glycan recognition receptors as M6PR. On a macroscopic level, this loss of molecular interactions translates into a reduced clearance from plasma when administrated intravenously. The reduced clearance of the protein could allow for less frequent dosing for the patients.

Example 7

In Vivo Plasma Clearance of Modified Sulfamidase Produced by New Method 1

Material and Methods

Plasma clearance (CL) of unmodified and modified recombinant sulfamidase produced as described in Example 1, in Quattromed Cell Factory (QMCF) episomal expression system (Icosagen AS) and modified according to the new method 1 of Example 4 was investigated in mice (C57BL/6J). The mice were given an intravenous single dose administration in the tail vein of 10 mg/kg sulfamidase and 10 mg/kg modified sulfamidase. Sulfamidase and modified sulfamidase were formulated at 2 mg/mL and administered at 5 mL/kg. Blood samples were taken from vena saphena or vena cava at different time points up to 24 h post dose (3 mice per time point). The blood was collected in EDTA tubes stored on ice and plasma was prepared by centrifugation. The plasma levels of sulfamidase and modified sulfamidase were analyzed by ECL. Plasma clearance was calculated using WinNonlin software version 6.3 (Non-compartmental analysis, Phoenix, Pharsight Corp., USA).

Quantification of Sulfamidase and Modified Sulfamidase by Electrochemiluminescence (ECL) Immunoassay:

Sulfamidase and modified sulfamidase in plasma PK samples were determined by ECL immunoassay using the Meso Scale Discovery (MSD) platform. A Streptavidin coated MSD plate was blocked with 5% Blocker-A in PBS. The plate was washed and different dilutions of standard and PK samples were distributed in the plate. A mixture of a biotinylated anti-sulfamidase mouse monoclonal antibody and Sulfo-Ru-tagged rabbit anti-sulfamidase antibodies was added and the plate was incubated at RT. Complexes of sulfamidase and labelled antibodies bind to the Streptavidin coated plate via the biotinylated mAb. After washing, the amount of bound complexes was determined by adding a read buffer to the wells and the plate was read in a MSD SI2400 instrument. The recorded ECL counts were proportional to the amount of sulfamidase in the sample and evaluated against a relevant sulfamidase standard.

Results

The plasma clearance in mice of modified sulfamidase was roughly 10-fold lower as compared to unmodified sulfamidase, see Table 3 below. This is probably at least partly due to the inhibition of receptor mediated uptake in peripheral tissue following chemical modification of sulfamidase (as demonstrated in the cellular uptake studies of Example 6).

The data on clearance in mice obtained for modified sulfamidase produced in the stable cell line according to Example 1 and modified according to new method 3 of Example 4, was in agreement with the data presented in Table 3 for modified sulfamidase produced in the QMCF system and modified by new method 1. The reduced clearance of the protein could allow for less frequent dosing for the patients.

TABLE 3

Plasma clearance of sulfamidase and modified sulfamidase

| Test article | Dose (mg/kg) | Plasma CL (L/(h · kg)) |
|---|---|---|
| sulfamidase (SEQ ID NO: 2) | 10 | 0.17 |
| modified sulfamidase (New method 1, SEQ ID NO: 2) | 10 | 0.014 |

Example 8

In Vivo Effect of Modified Sulfamidase on Brain Heparan Sulfate Storage

Materials and Methods

The effect of intravenously (i.v.) administered modified sulfamidase produced as described in Example 1, in Quattromed Cell Factory (QMCF) episomal expression system (Icosagen AS) and modified according to new method 1 of Example 4 on brain heparan sulfate storage in vivo was investigated.

Test Article Preparation:

Modified sulfamidase was formulated at 6 mg/mL, sterile filtrated and frozen at −70° C. until used. Frozen modified sulfamidase and corresponding vehicle solution were thawed on the day of injection at RT for minimum one hour up to two hours before use. Chlorpheniramine was dissolved in isotonic saline to a concentration of 0.5 mg/mL, and stored at −20° C.

Animals:

Male mice having a spontaneous homozygous mutation at the mps3a gene, B6.Cg-Sgsh$^{mps3a}$/PstJ (MPS IIIA)(Jackson Laboratories, ME, USA), were used. The animals were housed singly in cages at 23±1° C. and 40-60% humidity, and had free access to water and standard laboratory chow. The 12/12 h light/dark cycle was set to lights on at 7 pm. The animals were conditioned for at least two weeks before initiating the study. Wild-type siblings from the same breeding unit were also included as controls. In study A, mice were 23-24 weeks old whereas mice were 9-10 weeks old in study B.

Experimental Procedure Study A:

Modified sulfamidase at 30 mg/kg (n=8) and vehicle (n=7) were administered intravenously to MPS IIIA mice every other day for twenty-five days (13 injections). Chlorpheniramine was dosed (2.5 mg/kg) subcutaneously 30-45 min before administration of modified sulfamidase or vehicle. Dosing started approximately at 07.00 in the morning. The test article and vehicle were administered at 5 mL/kg. The final administration volume was corrected for the actual body weight at each dosing occasion. This scheme was repeated for vehicle. The study was finished 2 h after the last injection. Untreated age-matched wild-type mice (n=5) were included in conjunction with the test article-treated groups. The mice were anaesthetized by isoflurane. Blood was withdrawn from retro-orbital plexus bleeding. Perfusion followed by flushing 20 mL saline through the left ventricle of the heart. Tissues were dissected (brain, liver, spleen, lung, and heart), weighed and frozen rapidly in liquid nitrogen. The tissues and blood were prepared to measure hexosamine N-sulfate [α-1,4] uronic acid (HNS-UA) levels using LC-MS/MS. HNS-UA is a disaccharide marker of heparan sulfate storage, and thus a decrease in HNS-UA levels reflects degradation of heparan sulfate. The HNS-UA data were calculated in relative units vs. internal standard, expressed per mg tissue and normalized to the average of the control group. The data were analyzed by one-way ANOVA test and if overall significance was demonstrated also by Bonferroni's multiple comparison post-hoc test for test of significance between groups (*$P<0.05$, $P<0.01$, *$P<0.001$).

Experimental Procedure Study B:

Modified sulfamidase at 30 mg/kg (n=6), 10 mg/kg (n=6) and vehicle (n=6) were administered intravenously to MPS IIIA mice once weekly for 10 weeks (10 injections). Chlorpheniramine was dosed (2.5 mg/kg) subcutaneously 30-45 min before administration of modified sulfamidase or vehicle. The final administration volume was corrected for the actual body weight at each dosing occasion. This scheme was repeated for vehicle. The study was finished 24 h after the last injection. Untreated age-matched wild-type mice (n=6) were included in conjunction with the test article-treated groups. The mice were anaesthetized by isoflurane. Blood was withdrawn from retro-orbital plexus bleeding. Perfusion followed by flushing 20 mL saline through the left ventricle of the heart. Tissues were dissected (brain, liver, spleen), weighed and frozen rapidly in liquid nitrogen. The tissues and blood were prepared to measure HNS-UA levels using LC-MS/MS. The HNS-UA data were calculated in relative units vs. internal standard, expressed per mg tissue and normalized to the average of the control group. The data were analyzed by one-way ANOVA test and if overall significance was demonstrated also by Bonferroni's multiple comparison post-hoc test for test of significance between groups (*$P<0.05$, $P<0.01$, *$P<0.001$).

LC-MS/MS Analysis of HNS-UA in Tissue Samples:

Liquid chromatography tandem mass spectrometry (LC-MS/MS) analysis of hexosamine N-sulfate [α-1,4] uronic acid (HNS-UA) in tissue samples was conducted partly according to methods described by Fuller et al (Pediatr Res 56: 733-738 (2004)) and Ramsay et al (Mol Genet Metab 78:193-204 (2003)). The tissues (90-180 mg) were homogenized in substrate buffer (29 mM diethylbarbituric acid, 29 mM sodium acetate, 0.68% (w/v) NaCl, 100 mL water, pH 6.5) using a Lysing Matrix D device (MP Biomedicals, LLC, Ohio, US). Homogenization was performed for 25 s in a Savant FastPrep FP120/Bio101 homogenizer (LabWrench, ON, Canada) and the homogenate was subsequently centrifuged in an Eppendorf centrifuge 5417R at 10000 rcf. The supernatant was evaporated to near dryness. 150 µL derivatizing solution (250 mM 3-methyl-1-phenyl-2-pyrazolin-5-one (PMP), 400 mM $NH_3$, pH 9.1) and 5 µL of the internal standard Chondroitin disaccharide Δdi-4S sodium (ΔUA-GalNAc4S, 0.1 mg/mL) stock solution was added. The derivatization was performed at 70° C. for 90 min under agitation and then the solutions were acidified with 200 µL of 800 mM formic acid. Deionized water was added to the samples to a final volume of 500 µL, and extraction was performed with chloroform (3×500 µL) to remove excess PMP. Centrifugation was performed at 13000×g for 5 min and the upper phase was transferred to a new vial. To remove any excess of formic acid and $NH_4COOH$, the aqueous phase was evaporated to dryness in a speed vac (Savant Instruments Inc., Farmingdale, N.Y.), The samples were reconstituted to a total of 100 µL of 5% acetonitrile/0.1% acetic acid/0.02% TFA.

LC-MS/MS analysis was performed on Waters Ultra Performance Liquid Chromatography (UPLC), coupled to Sciex API 4000 triple quadrupole mass spectrometer. Instrument control, data acquisition and evaluation were done with Analyst software.

LC separation was performed by the use of an Acquity C18 CSH column (50×2.1 mm, 1.7 µm). Mobile phase A consisted of 5% acetonitrile/0.5% formic acid, and mobile phase B consisted of 95% acetonitrile/0.5% formic acid. A gradient from 1% to 99% B in 7 min was used at a flow rate of 0.35 mL/min. The injection volume was 10 µL. The API 4000 was operated in electrospray negative ion multiple reaction monitoring (MRM) mode. The ion spray voltage was operated at 4.5 kV, and the source temperature was 450° C. Argon was used as collision gas. Collision energy was 34 V. The MRM transitions were 764.4/331.2 (PMP-HNS-UA) and 788.3/534.3 (PMP-internal standard). The relative amount of the HNS-UA was calculated with respect to the level of the internal standard.

Results

Figure 6A:
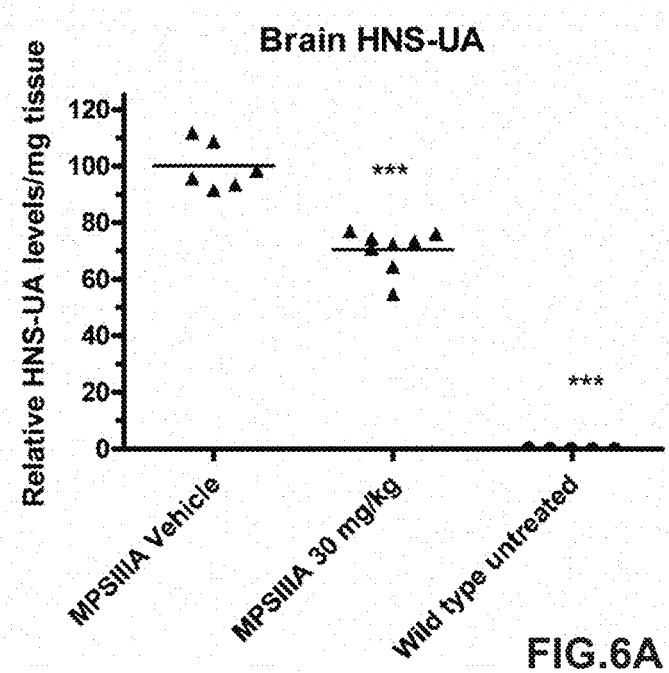
FIG. 6A shows the results from in vivo treatment of MPS IIIA deficient mice. The diagram shows clearance of heparan sulfate storage in the brain of mice after i.v. dosing every other day (13 doses) of sulfamidase modified according to new method 1 at 30 mg/kg.

The results from study A shown in FIG. 6A illustrates that sulfamidase modified according to the new method 1 decreased the levels of HNS-UA in the brain by 30% following repeated intravenous administration every other day for 25 days (13 doses) at 30 mg/kg.

Figure 6B:
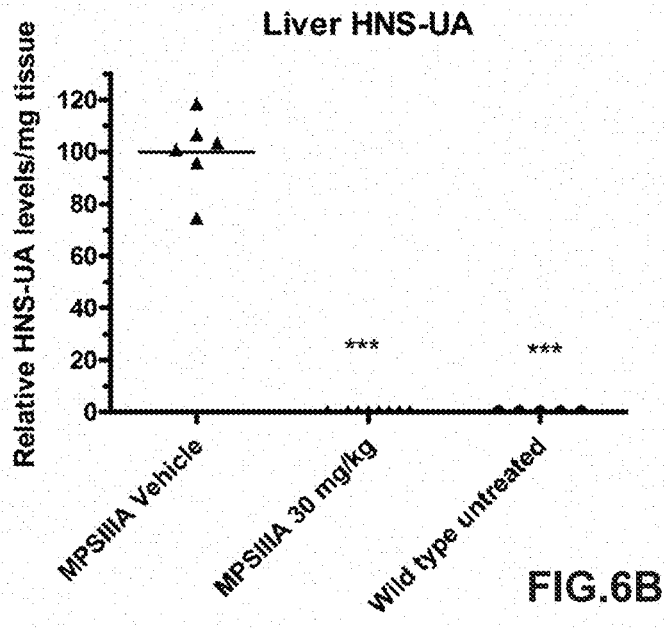
FIG. 6B shows the results from in vivo treatment of MPS IIIA deficient mice. The diagram shows clearance of heparan sulfate storage in the liver of mice after i.v. dosing every other day (13 doses) of sulfamidase modified according to new method 1 at 30 mg/kg.

In addition, treatment with the modified sulfamidase totally abolished HNS-UA levels in liver (FIG. 6B) and lung (not shown).

Figure 6C:
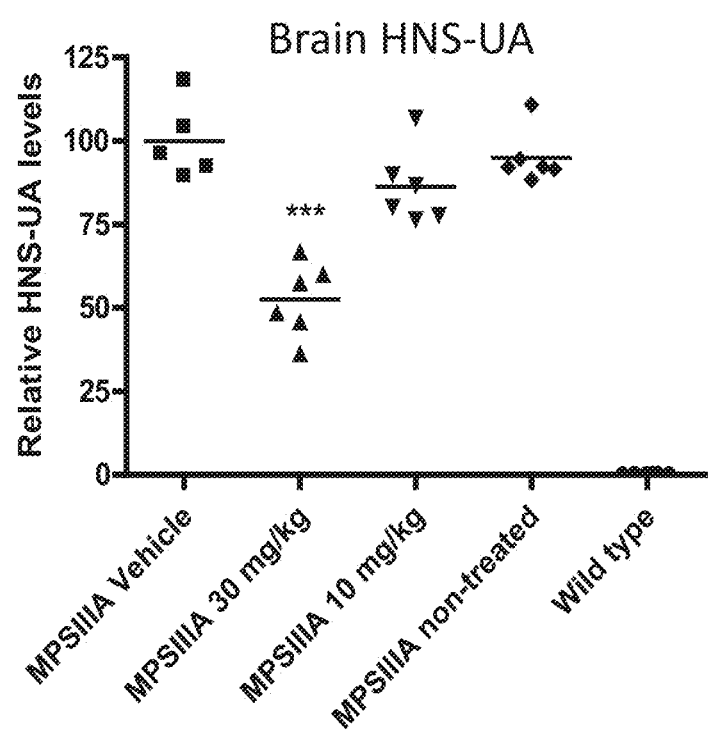
FIG. 6C shows the results from in vivo treatment of MPS IIIA deficient mice. The diagram shows clearance of heparan sulfate storage in the brain of mice after i.v. dosing once weekly (10 doses) of sulfamidase modified according to new method 1 at 30 mg/kg and 10 mg/kg, respectively.
Figure 7:
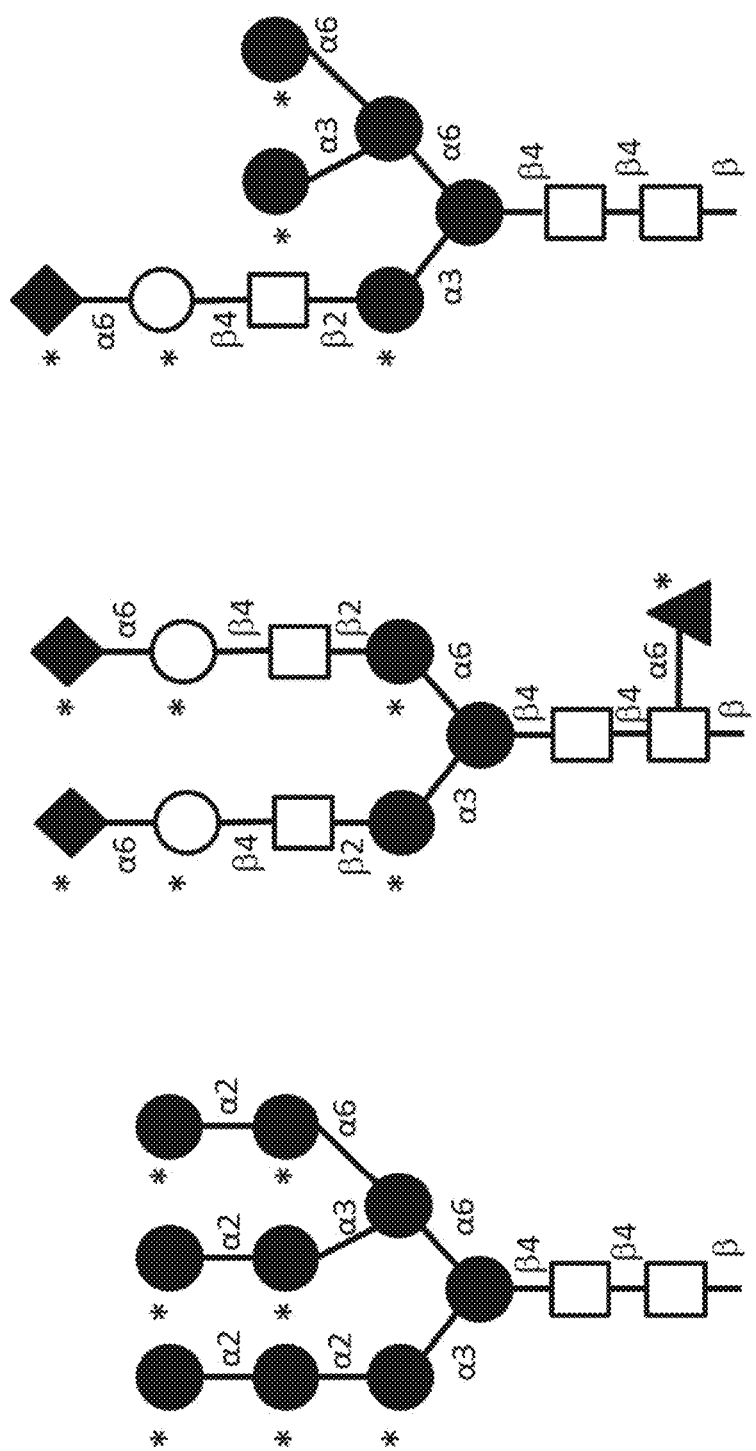
FIG. 7 is a schematic drawing of the three archetypal N-glycan structures generally present in proteins. The left glycan represents the oligomannose type, the middle the complex type, and the right one the hybrid type. In the Figure the following compounds are depicted: black filled diamonds correspond to N-acetylneuraminic acid; black filled circles correspond to mannose; squares correspond to N-acetylglucosamine; black filled triangle corresponds to fucose; circle corresponds to galactose. Sugar moieties marked with an asterisk can be modified by the periodate/borohydride treatment disclosed herein.

The results from study B are shown in FIG. 6C and illustrates that modified sulfamidase according to the new method 1 decreased the levels of HNS-UA in the brain by 48% and 14% following repeated intravenous administration once weekly for 10 weeks at 30 mg/kg and 10 mg/kg, respectively.

These results thus demonstrate that a sulfamidase protein modified according to the new method 1 described herein causes, after long-term treatment, a robust reduction of HNS-UA levels in brain as well as an essentially complete reduction of HNS-UA levels in peripheral organs.

Example 9

Optimization of Sulfamidase Modification

The chemical modification process can generally be divided into two parts where the oxidation step is the first step, denoted R1 hereinafter, and the reduction is the second step, denoted R2. To optimize the two steps a full factor design of experiment (DoE) investigating the effect of temperature, concentration and time for the two steps was set up.

Materials and Methods

Sulfamidase produced as described in Example 1 in Quattromed Cell Factory (QMCF) episomal expression system (Icosagen AS) were modified essentially as described in Example 4 for new method 1, however parameters subjected to investigation were varied in accordance with Table 4 (below). The investigation of R1 was carried out with the same reduction and parameters work-up as described in Example 4 (method 1). The end-points for the analysis are degree of oxidation of glycans described in Example 1, and the level of cell uptake of the modified protein, described in Example 6.

TABLE 4

| Parameters varied in R1 and R2 | | |
|---|---|---|
| Variable | R1 | R2 |
| T (° C.) | 0, 8, 22 | 0, 8, 22 |
| t (min) | 30, 60, 120 | 30, 60, 120 |
| c (mol/L) | 10, 20, 40 | 1.2x (c in R1), 2.5x (c in R1), 5x (c in R1) |

The number of parameters and the type of design selected yields ten experiments for each step, the results of which were evaluated using the MODDE 10 software (Umetrics AB).

In addition the influence of the second quenching step was tested on sulfamidase produced with the R1 parameters 8° C., 60 min and 20 mM sodium meta-periodate. Two additional reactions were run in parallel to the DoE experiment and quenched using 0.1 M acetone or by addition of acetic acid until a pH of 6.0 or lower was obtained. The final work-up followed the scheme for the other reactions. The sulfamidase thus produced was evaluated using the SDS-PAGE method described in Example 5.

The R2 experiments were conducted with sulfamidase modified according to the parameters found to be optimal after the analysis of the DoE of R1.

Results

The R1 results are summarized in table 5 below:

TABLE 5

| R1 experiments and results | | | | | | | |
|---|---|---|---|---|---|---|---|
| Varied parameters | | | Remaining original (natural) N-Glycan (%) | | | | Cell uptake % of unmodified |
| T (° C.) | t (min) | c (mmol/L) | N (21) | N (131) | N (244) | N (393) | sulfamidase uptake |
| 0 | 30 | 10 | 0 | 0.9 | 0 | 0 | 12 |
| 0 | 120 | 10 | 0 | 0.4 | 0 | 0 | 9.5 |
| 22 | 30 | 10 | 0 | 0.2 | 0 | 0 | 7.1 |
| 22 | 120 | 10 | 0 | 0.1 | 0 | 0 | 8.5 |
| 0 | 30 | 40 | 0 | 0.3 | 0 | 0 | 3.8 |
| 0 | 120 | 40 | 0 | 0.1 | 0 | 0 | 3.5 |
| 22 | 30 | 40 | 0 | 0.1 | 0 | 0 | 2.7 |
| 22 | 120 | 40 | 0 | 0.01 | 0 | 0 | 3.5 |
| 8 | 60 | 20 | 0 | 0.2 | 0 | 0 | 6.1 |
| 8 | 60 | 20 | 0 | 0.2 | 0 | 0 | 6.5 |

In addition, a glycosylation analysis according to Example 1 was conducted for sulfamidase modified according to the known method. No remaining original N-glycans were detected at the N-glycosylation sites N(21), N(131), N(244), and N(393).

The MODDE evaluation of R1 (oxidation) showed that an optimum for R1 at a temperature of around 8° C., a reaction duration of around 1 h and a concentration of around 10 mmol/L of sodium meta-periodate. The overall protein health (e.g. structural integrity) seems to benefit from the lowest oxidant concentration as possible that still limits the cellular uptake via glycan recognition receptors to the level of new method 1 (see Example 6 for details).

Among the various conditions disclosed for R1 reaction time was considered as an important parameter for degree of glycan modification. In addition, periodate concentration may influence degree of glycan modification.

The R2 (reduction) design thus used the above identified preferred parameters for R1, i.e. used for oxidation of sulfamidase. The critical end-point for R2 is FGly content since it was found to influence the activity of the modified sulfamidase (cf Examples 3 and 5). See Table 6 below for results. The relative amount of the peptide fragments containing FGly50 and Ser50 was analyzed with LC-MS by measuring the peak areas from reconstructed ion chromatograms (without correction for ionization efficiency).

TABLE 6

Summary of DoE for R2 and confirmatory experiments

| Varied parameters | | | Active site | |
|---|---|---|---|---|
| t (min) | T (° C.) | c (mmol/L) | Ser formation (%) | FGly/Ser Ratio |
| 30 | 0 | 12 | 10 | 9.0 |
| 90 | 0 | 12 | 11 | 8.1 |
| 30 | 22 | 12 | 15 | 5.7 |
| 90 | 22 | 12 | 17 | 4.9 |
| 30 | 0 | 50 | 40 | 1.5 |
| 90 | 0 | 50 | 50 | 1.0 |
| 30 | 22 | 50 | 64 | 0.6 |
| 90 | 22 | 50 | 72 | 0.4 |
| 60 | 8 | 25 | 42 | 1.4 |
| 30 | 0 | 20 | 25 | 3.0 |
| 30 | 0 | 50 | 45 | 1.2 |
| 60 | 0 | 15 | 15 | 5.7 |
| 60 | 0 | 25 | 33 | 2.0 |
| 60 | 8 | 12 | 15 | 5.7 |
| 60 | 8 | 50 | 62 | 0.6 |

The DoE for R2 showed that the Ser formation is related to concentration of sodium borohydride and temperature. Taking into account Ser formation and the presence of high molecular weight forms (data not shown, the results are analogous with the ones received for new method 2 in Example 4), the preferred conditions for R2 are a temperature of around 0° C., a reaction duration of around 1 h or less, and a sodium borohydride concentration of more than 12 mmol/L and up to and including 50 mmol/L.

It was confirmed on SDS-PAGE (data not shown) that the sulfamidase produced in a reaction where the reduction step was quenched was comparable with the sulfamidase produced without quenching. This indicates that the introduction of the second quenching step do not negatively affect the quality of the material by either quenching with 0.1 M acetone or by lowering the pH to below 6 by addition of acetic acid.

Example 10

Analysis of Glycan Structure after Chemical Modification of Sulfamidase According to Previously Known Method Material and Methods
Chemical Modification According to the Known Method:
The chemical modification of sulfamidase according to the known method was performed as described in Example 2.
Glycosylation Analysis:
The analysis of glycan structure on sulfamidase after chemical modification was performed according to the LC-MS method described in Example 1.
Resulting modifications on the glycan moieties on the four tryptic peptide fragments containing the N glycosylation sites N(21), N(131), N(244) and N(393) described in Example 1 were investigated by LC-MS analysis.
Results
Glycosylation Analysis:
As described in Example 1, the type of glycosylation found on the four glycosylation sites prior to the chemical modification was predominantly complex glycans on N(21) and N(393), and oligomannose type of glycans on N(131) and N(244).

After the chemical modification, detailed characterization of the modified glycan structure was performed on the most abundant chemically modified glycopeptides (less abundant glycans were not detectable due to significant decrease in sensitivity as a result of increased heterogeneity of the glycans after chemical modification). In this Example, the modification on Man-6 glycan after chemical modification according to the known method is investigated.

Figure 8A:
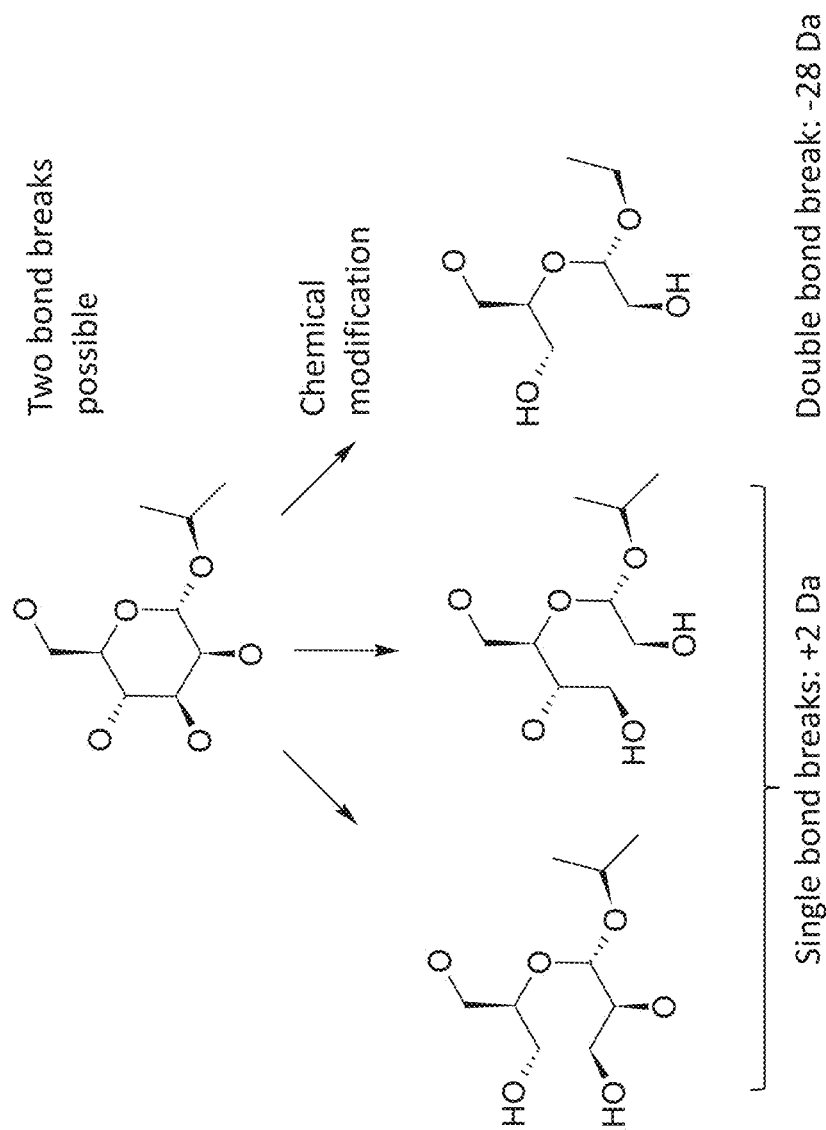
FIG. 8A is a schematic drawing illustrating predicted bond breaks on mannose after chemical modification.
Figure 8B:
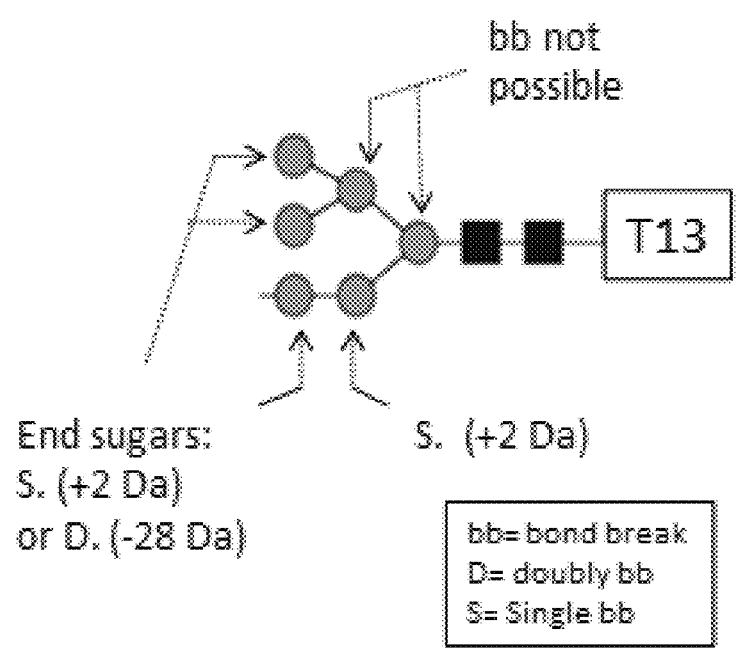
FIG. 8B is a schematic drawing illustrating a model of a Man-6 glycan. The sugar moieties susceptible to bond breaks upon oxidation with periodate are indicated. Grey circles correspond to mannose, black squares correspond to N-acetylglucosamine, T13 corresponds to the tryptic peptide NITR with the N-glycosylation site N(131) included.
Figure 9A:
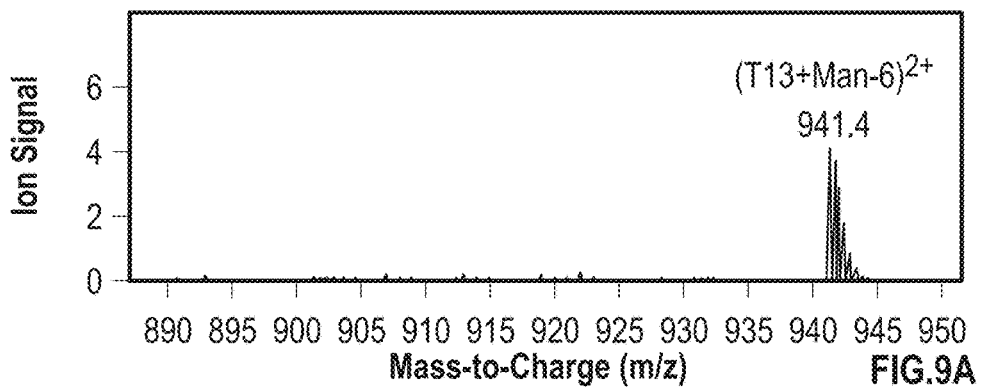
FIGS. 9A-9D represent mass spectra of doubly charged ions corresponding to tryptic peptide T13 with Man-6 glycan attached to N(131) (T13+Man-6 glycan), prior to (FIG. 9A) and after chemical modification (FIG. 9B-D) according to previously known method (S.=single bond breaks; D.=double bond breaks; e.g. D.x3=3 double bond breaks).
Figure 9B:
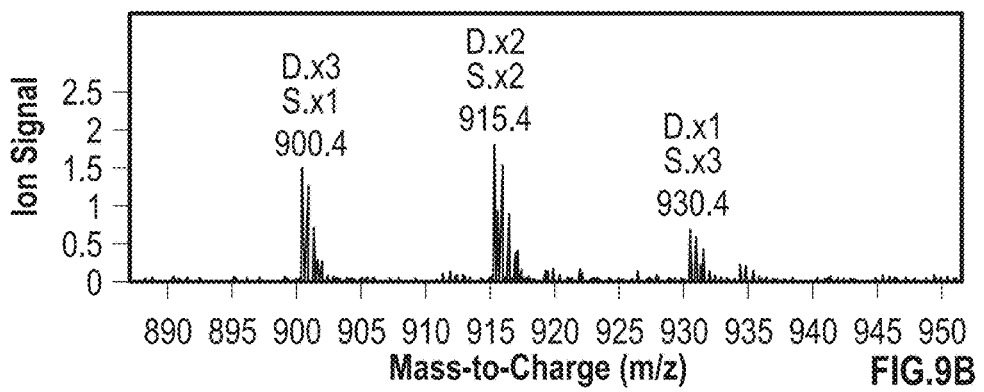
Figure 9C:
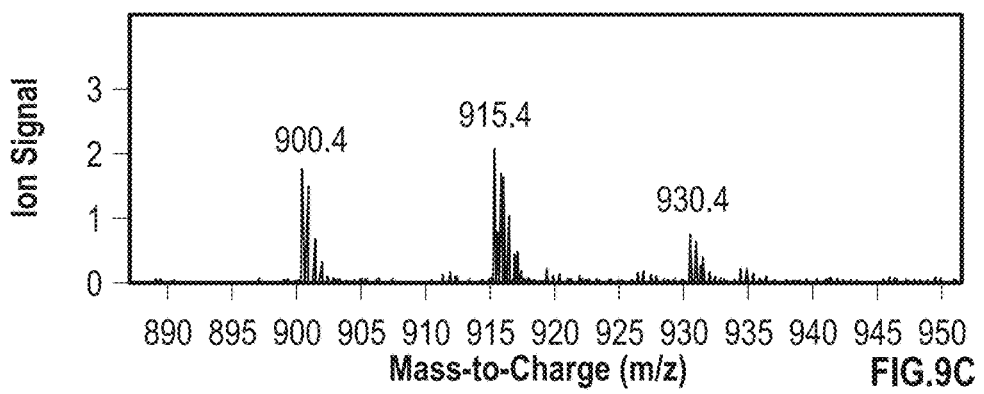
Figure 9D:
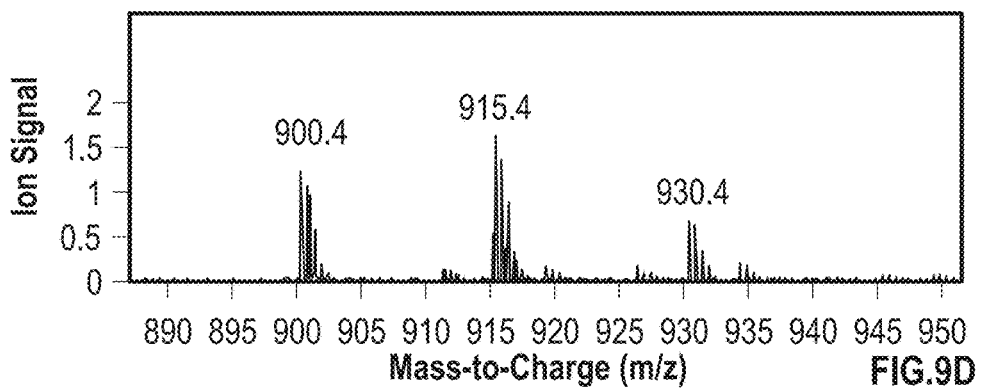

Periodate treatment of glycans cleaves carbon bonds between two adjacent hydroxyl groups of the carbohydrate moieties and alter the molecular mass of the glycan chain. FIG. 8A illustrates an example of predicted bond breaks on mannose after chemical modification. FIG. 8B depicts a model of Man-6 glycan showing the theoretical bond breaks that may take place after oxidation with sodium periodate.

Figure 10A:
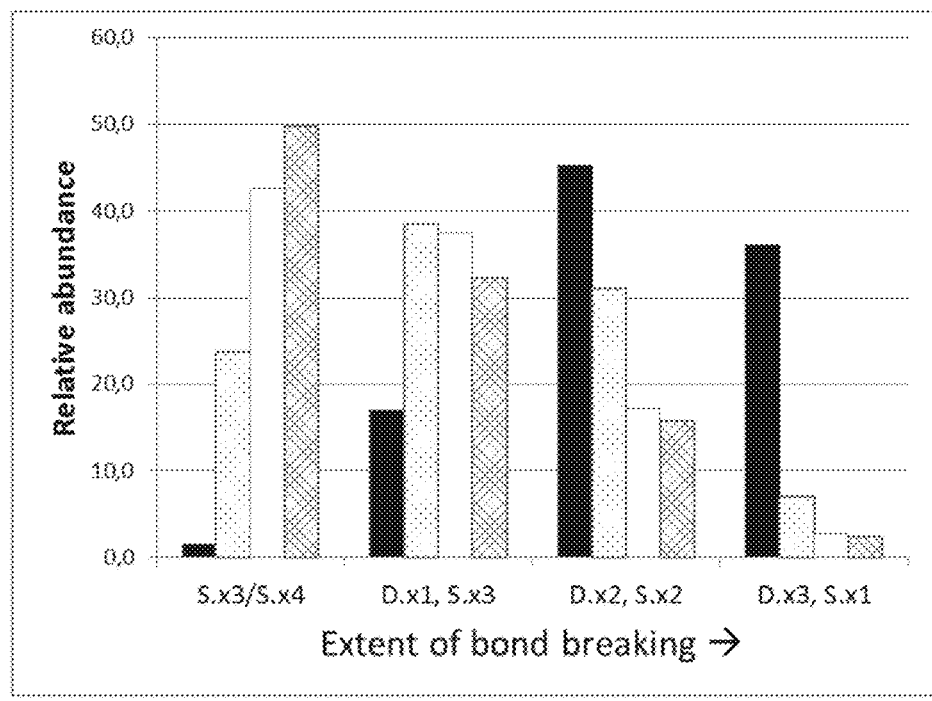
FIG. 10A is a diagram visualizing the extent of bond breaking of the tryptic peptide T13+Man-6 glycan after chemical modification according to the previously known method (black bar), new method 1 (black dots), new method 3 (white), and new method 4 (cross-checkered).

In FIGS. 9A-9D are shown mass spectra of the tryptic peptide NITR with Man-6 glycan attached to N(131) (T13+ Man-6 glycan), prior to and after chemical modification according to the previously known method. Ions corresponding to the chemically modified glycopeptide with various degree of bond breaking were identified. For Man-6 glycan, there can theoretically be a maximum of 3 double bond breaks and one single bond break. When the modification was performed according to the known method, the most intense ion signal in the mass spectrum was found to be corresponding to 2 double bond breaks and 2 single bond breaks, while the second most intense ion signal corresponded to 3 double bond breaks and one single bond break, which is the most extensive bond breaks possible. A diagram visualizing the extent of bond breaking found on T13+ Man-6 glycan after chemical modification according to the known method is shown in FIG. 10A (due to isotopic distribution from the ions observed, the results are approximative but comparable). The reproducibility of the chemical modification was tested by using three different batches of chemically modified sulfamidase produced according to the previously known method. The ions corresponding to different degree of bond breaking showed very similar distribution in the MS spectra from the three different batches.

Example 11

Analysis of Glycan Structure after Chemical Modification of Sulfamidase According to New Methods 1, 3, and 4

New Methods 1, 3, and 4:

The chemical modifications of sulfamidase according to the new methods were performed as described in Example 4.

Glycosylation Analysis:

The glycosylation analysis was performed according to the LC-MS method described in Example 1. Resulting modifications on the glycan variants of the four tryptic peptide fragments containing the N glycosylation sites N(21), N(131), N(244) and N(393) were investigated by LC-MS analysis.

Results

Glycosylation Analysis:

Detailed characterization of the modified glycan profile on sulfamidase, chemically modified according to new methods 1, 3, and 4, was performed on the most abundant chemically modified glycopeptides. In this Example 11, the modification on Man-6 glycan after chemical modification according to new methods 1, 3, and 4, was investigated.

Ions corresponding to the chemically modified glycopeptide T13+Man-6 glycan with various degree of bond breaking were identified. Theoretically there can be a maximum of 3 double bond breaks and one single bond break (see FIG. 8B a model of Man-6 glycan showing the bond breaks possible to occur after oxidation with sodium periodate). When the modification was performed according to the new method 1, the most intense ion signal in the mass spectrum was found to be corresponding to one double bond break and 3 single bond breaks, while the second most intense ion signal corresponded to 2 double bond breaks and 2 single bond breaks. When the modification was performed according to new methods 3 and 4, the bond breaks on Man-6 glycan were even further shifted to preferentially single bond breaks. In FIG. 10A is shown a diagram visualizing the extent of bond breaking of the tryptic peptide T13+Man-6 glycan after chemical modification.

The reproducibility of the chemical modification was tested by using triplicates (new method 1) or duplicates (new methods 3) of chemically modified sulfamidase.

When comparing the Man-6 glycan modifications resulting from sulfamidase chemically modified according to the known method with the Man-6 glycan modifications resulting from sulfamidase chemically modified according to the new methods 1, 3, and 4, there was a large difference in degree of bond breaking. This is illustrated in FIG. 10A, where the distribution of the different degrees of bond breaking is plotted for the four methods (due to isotopic distribution from the ions observed, the results are approximative, but comparable).

Figure 10B:
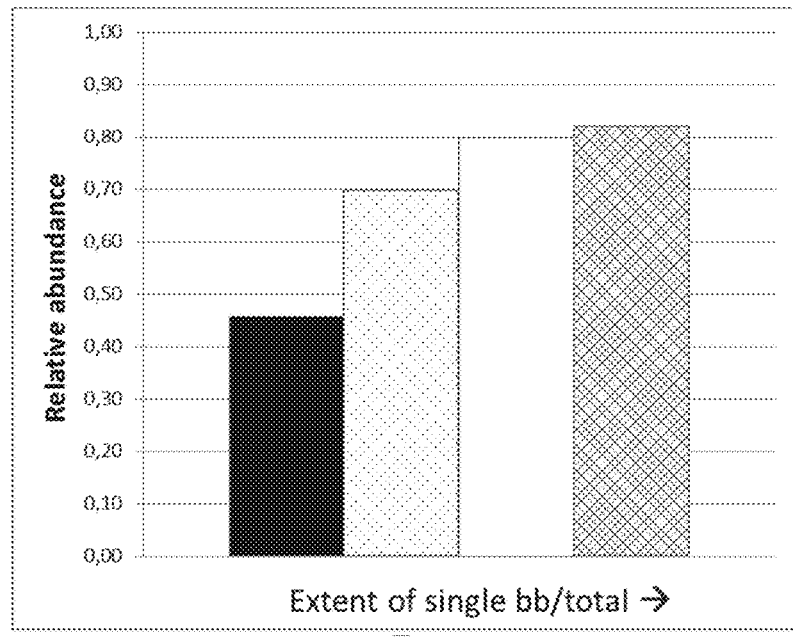
FIG. 10B is a diagram visualizing the relative abundance of single bond breaks in the tryptic peptide T13+Man-6 glycan after chemical modification according to the previously known method (black bar), new method 1 (black dots), new method 3 (white), and new method 4 (cross-checkered).

FIG. 10B shows the relative abundance of single bond breaks for the methods used. The previously known method provides a modified sulfamidase having 45% single bond breaks in the investigated Man-6-glycan, while the new methods 1, 3, and 4 have 70, 80, and 82% single bond breaks, respectively, after chemical modification.

The invention claimed is:

1. A method of preparing a modified sulfamidase, said method comprising:
   a) reacting a glycosylated sulfamidase with an alkali metal periodate,
   a2) optionally quenching the reaction resulting from step a), and
   b) reacting said sulfamidase with an alkali metal borohydride for a time period of no more than 2 h,
   wherein the steps are performed in sequence without performing an intermediate step.

2. The method according to claim 1, and wherein the concentration of said alkali metal borohydride is between 10 and 80 mM.

3. The method according to claim 1, wherein step a) is performed for a time period of no more than 4 h.

4. The method according to claim 1, wherein step a) is further characterized by at least one of i)-iii):
   i) said alkali metal periodate is sodium meta-periodate;
   ii) the concentration of said alkali metal periodate is no more than 20 mM, and
   iii) said reaction is performed at a temperature of between 0 and 22° C.

5. The method according to claim 1, wherein said reacting of step a) is performed at a pH of 3-7.

6. The method according to claim 1, wherein step b) is further characterized by at least one of i)-iv):
   i) said alkali metal borohydride is sodium borohydride;
   ii) the concentration of said alkali metal borohydride is no more than 4 times the concentration of said alkali metal periodate;
   iii) said reaction is performed for a time period of no more than 1.5 h, and
   iv) said reacting is performed at a temperature of between 0 and 8° C.

7. The method according to claim 1, wherein each of step a) and step b) is individually performed for a time period of no more than 2 h, and said alkali metal borohydride is optionally used at a concentration of 0.5-4 times the concentration of said alkali metal periodate.

8. The method according to claim 1, wherein step a) is performed for a time period of no more than 3 h, and step b) is performed for a time period of no more than 1 h, and said alkali metal borohydride optionally is used at a concentration of no more than 4 times the concentration of said alkali metal periodate.

9. The method according to claim 1, wherein the method comprises step a2) after step a), wherein the reaction resulting from step a) is quenched.

10. The method according to claim 1, further comprising a step b2) after step b), wherein the reaction resulting from step b) is quenched.

11. The method according to claim 1, wherein said glycosylated sulfamidase comprises glycan moieties at at least four asparagine residues.

12. The method according to claim 11, wherein said alkali metal periodate oxidizes cis-glycol groups of the glycan moieties to aldehyde groups.

13. The method according to claim 12, wherein said alkali metal borohydride reduces said aldehydes to alcohols.

* * * * *